United States Patent
Luan et al.

(10) Patent No.: US 9,360,454 B2
(45) Date of Patent: Jun. 7, 2016

(54) METHODS AND KITS FOR DETECTION OF COENZYME Q10

(71) Applicant: Berg LLC, Nashville, TN (US)

(72) Inventors: Shen Luan, Franklin, MA (US); Niven Rajin Narain, Cambridge, MA (US); Rangaprasad Sarangarajan, Boylston, MA (US); Nikunj Narendra Tanna, Boston, MA (US)

(73) Assignee: Berg LLC, Nashvillle, TN (US)

( * ) Notice: Subject to any disclaimer, the term of this patent is extended or adjusted under 35 U.S.C. 154(b) by 0 days.

(21) Appl. No.: 13/783,205

(22) Filed: Mar. 1, 2013

(65) Prior Publication Data

US 2014/0038302 A1    Feb. 6, 2014

Related U.S. Application Data

(60) Provisional application No. 61/606,019, filed on Mar. 2, 2012.

(51) Int. Cl.
| | |
|---|---|
| *G01N 27/62* | (2006.01) |
| *G01N 27/00* | (2006.01) |
| *C07F 3/00* | (2006.01) |
| *G01N 33/82* | (2006.01) |

(52) U.S. Cl.
CPC ............... *G01N 27/62* (2013.01); *G01N 33/82* (2013.01); *G01N 2458/15* (2013.01); *G01N 2560/00* (2013.01); *Y10T 436/20* (2015.01); *Y10T 436/200833* (2015.01)

(58) Field of Classification Search
CPC .......... G01N 27/62; G01N 27/00; C02F 3/00; Y10T 436/20; Y10T 436/200833
USPC ........... 436/128, 127; 73/61.58, 61.52, 61.43, 73/61.41, 53.01
See application file for complete search history.

(56) References Cited

U.S. PATENT DOCUMENTS 3,769,170 A    10/1973    Kondo et al.

FOREIGN PATENT DOCUMENTS

EP    1466983 A1    10/2004

OTHER PUBLICATIONS

Lagendijk Jennifer et al, Measurement of the ratio between the reduced and oxidized forms fo coenzyme Q10 in human plasma as a possible marker of oxidative stress, Journal of Lipid Research, vol. 37, 1996, pp. 67-75.*
Ruiz-Jimenez J. et al, Determination of the ubiquinol-10 and ubiquinone-10 (coenzyme Q10) in human serum by liquid chromatography tandem mass spectrometry to evaluate the oxidative stress, Journal of chromatography A, Dec. 21, 2007, 1175:2, pp. 242-248.*
Mosca Fabrizio et al, Assay of Coenzyme Q10 in Plasma by a Single Dilution Step, Analytical Biochemistry, 2002, 305, 49-54.*
International Search Report, obtained on Aug. 4, 2014, pp. 1-2.*
International Search Report in PCT/US13/28764, date of mailing May 13, 2013.
Li, L., et al., "Urinary excretion study of coenzyme Q10 in rats by ultra-performance liquid chromatography-mass spectrometry," *Journal of Chromatograpic Science*, vol. 46, pp. 215-219, 2008.
Tang, P.H. et al., "Measurement of reduced and oxidized coenzyme Q9 and coenzyme Q10 levels in mouse tissues by HPLC with coulometric detection," *Clinica Chimica Acta*, vol. 341, pp. 173-184, 2004.
Tomono, Y. et al., "Pharmacokinetic study of deuterium-labelled coenzyme Q10 in man," *Int J Clin Pharmacol Ther Toxicol*, vol. 24, No. 10, pp. 536-541, 1986.
Xue, X., et al., "Analysis of coenzyme Q10 in bee pollen using online cleanup by accelerated solvent extraction and high performance liquid chromatography," *Food Chemistry*, vol. 133, pp. 573-578, 2012.
Hansen, G. et al., "Sensitive and selective analysis of coenzyme Q10 in human serum by negative APCI LC-MS," *The Analyst*, vol. 129, pp. 45-50, 2004.
Tang P.H. et al., "HPLC analysis of reduced and oxidized coenzyme Q(10) in human plasma", *Clinical Chemistry*, vol. 47, Issue 2, pp. 256-65, 2001.

* cited by examiner

*Primary Examiner* — Christine T Mui
(74) *Attorney, Agent, or Firm* — McCarter & English, LLP; Elizabeth A. Hanley, Esq.; Jill Mello

(57) ABSTRACT

The invention provides methods for rapid and quantitative extraction and detection of coenzyme Q10 in a sample readily adaptable to high throughput screening methods. The invention further provides reagents and kits for practicing the methods of the invention.

82 Claims, 14 Drawing Sheets

Figure 1: Standard curve for CoQ10 at O.D. 275 nm.
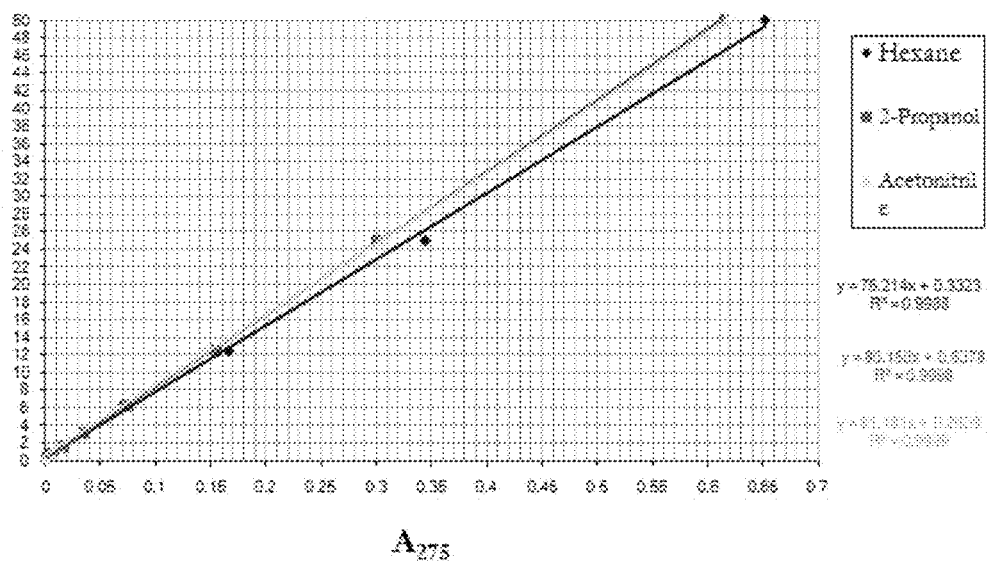
Figure 2: Standard curve for CoQ10 at O.D. 275 nm
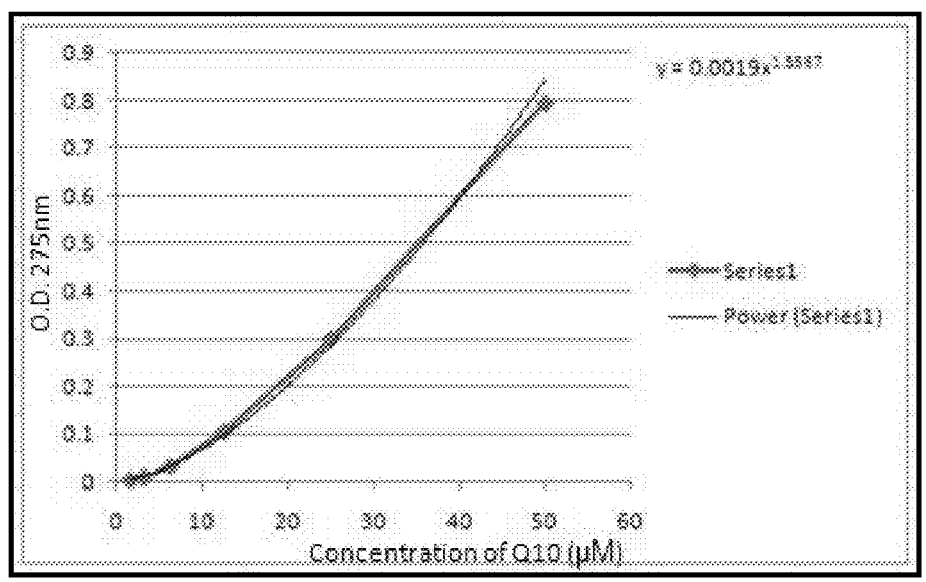

Figure 3A: CoQ10 in untreated HepG2 Cells
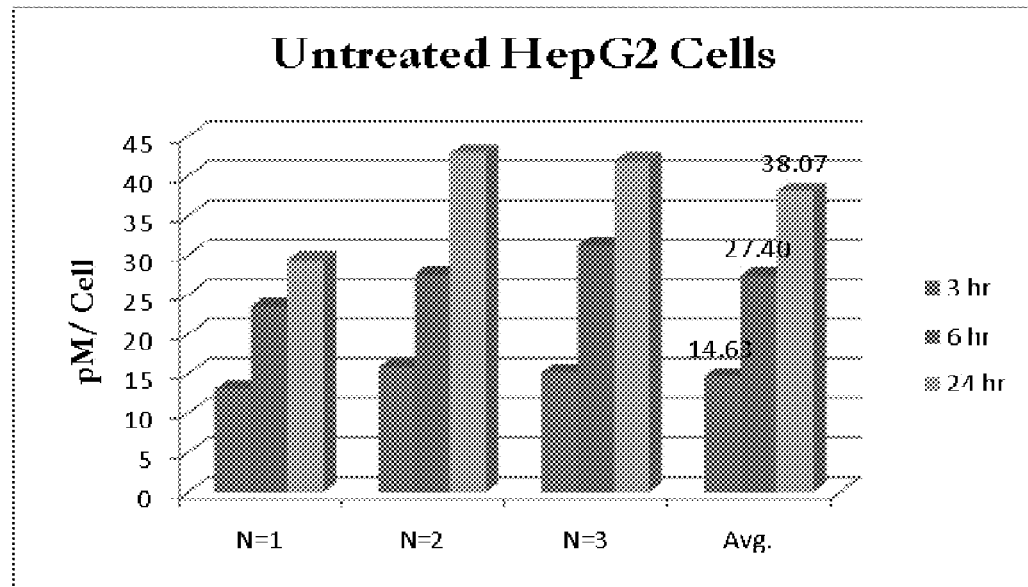
Figure 3B: CoQ10 levels in HepG2 cells treated with CoQ10 solubilized in 2-propanol (50μM)
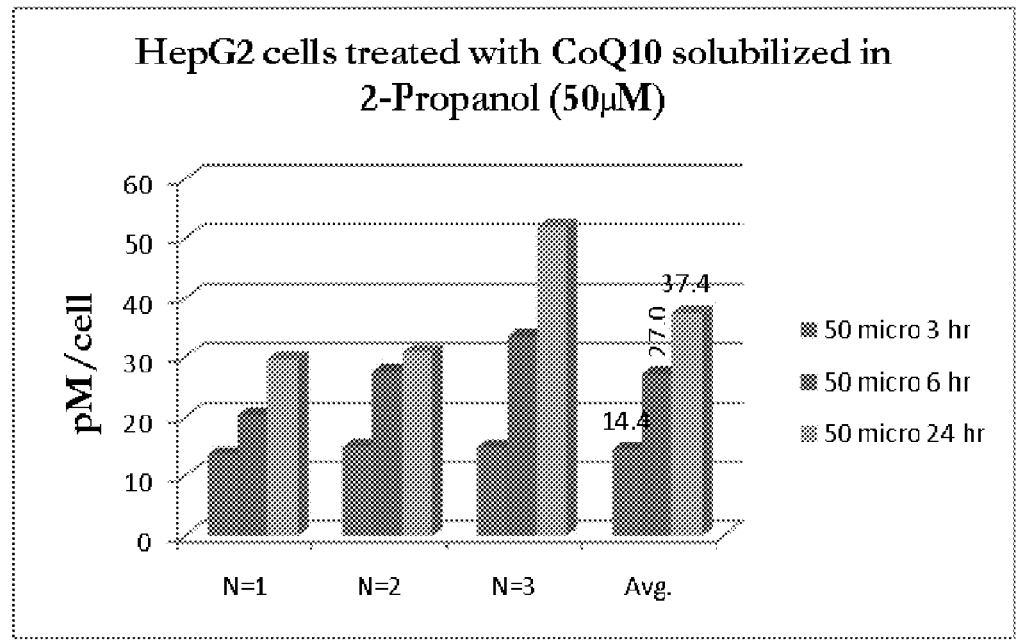

Figure 3C: CoQ10 levels in HepG2 cells treated with CoQ10 solubilized in 2-propanol (100μM)
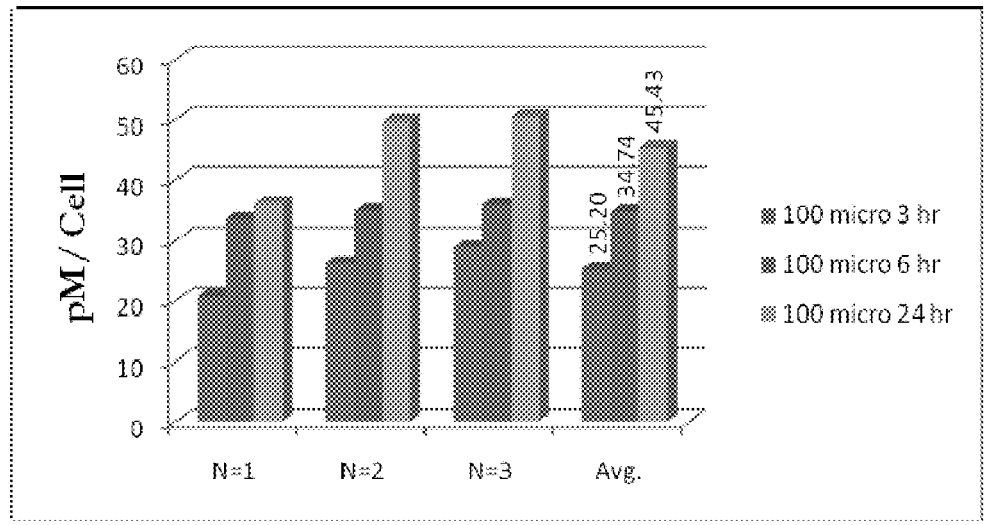
Figure 3D: Levels of HepG2 cells treated with CoQ10 nanoemulsion/suspension (50μM)
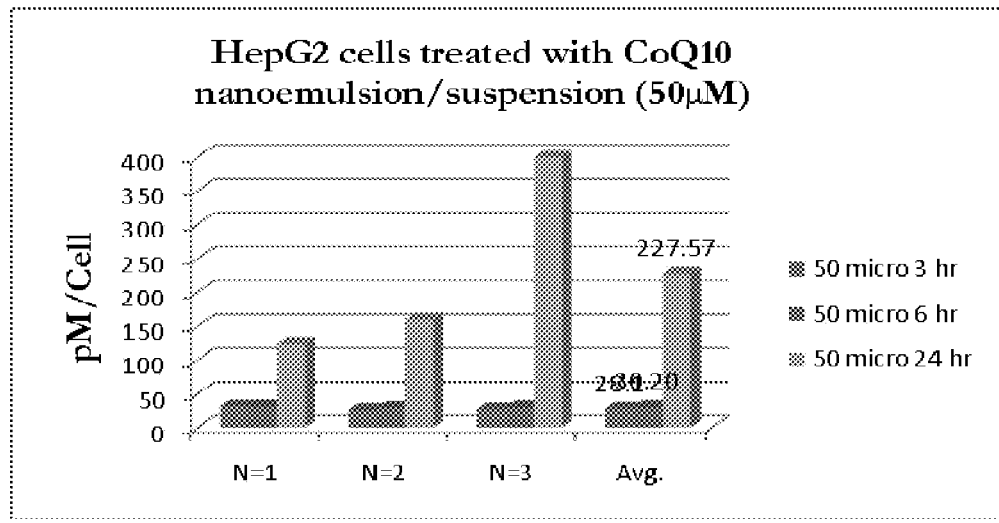

Figure 3E: Levels of HepG2 cells treated with CoQ10 nanoemulsion/suspension (100μM)
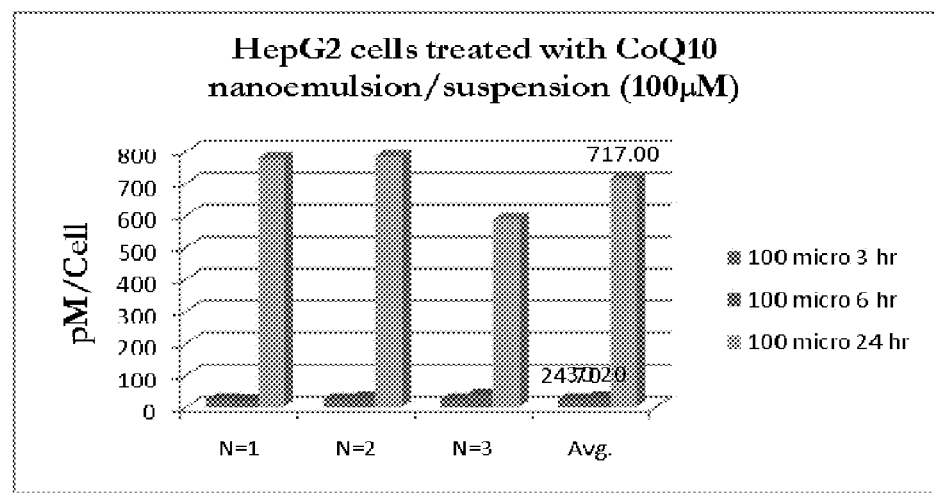

Figure 4: Standard curves for CoQ10- and CoQ10H$_2$, with samples prepared using hexane as a diluent and hexane-reconstituted CoQ10- and CoQ10H$_2$ stocks.
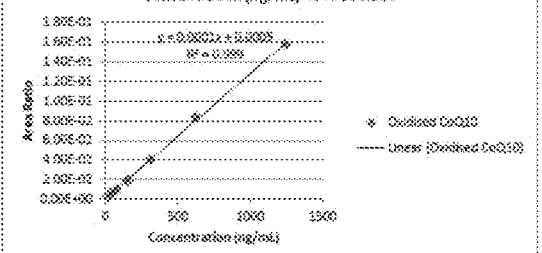
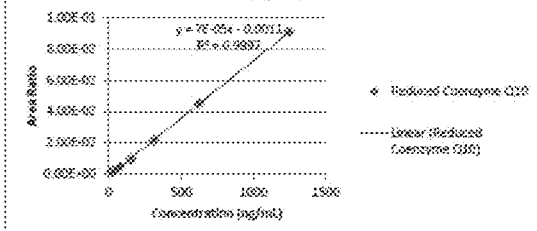

Figure 5: Standard curves for CoQ10- and CoQ10H$_2$, with samples prepared using water as a diluent and methanol-reconstituted CoQ10- and CoQ10H$_2$ stocks.
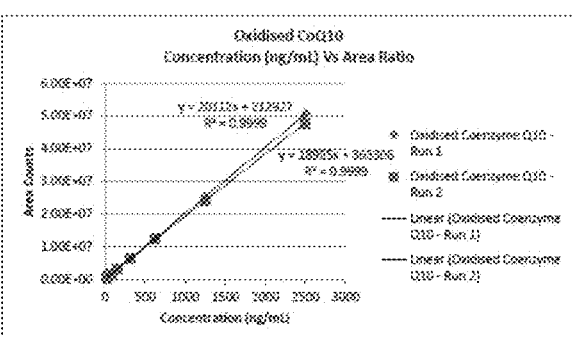
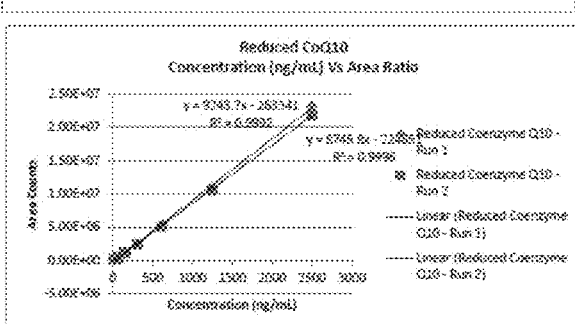

Figure 6. Standard curve and representative chromatograms for total CoQ10 in plasma samples.
Standard Curve
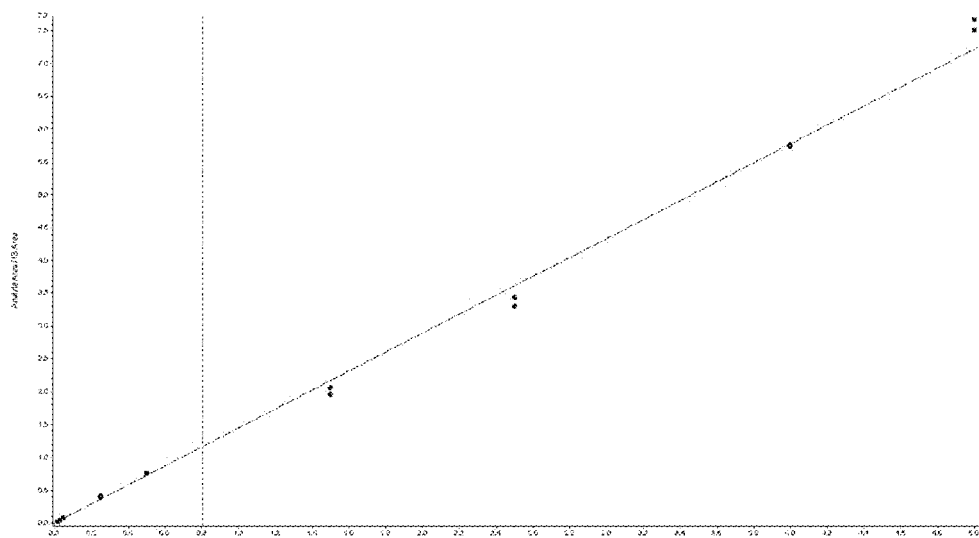
Representative Chromatogram
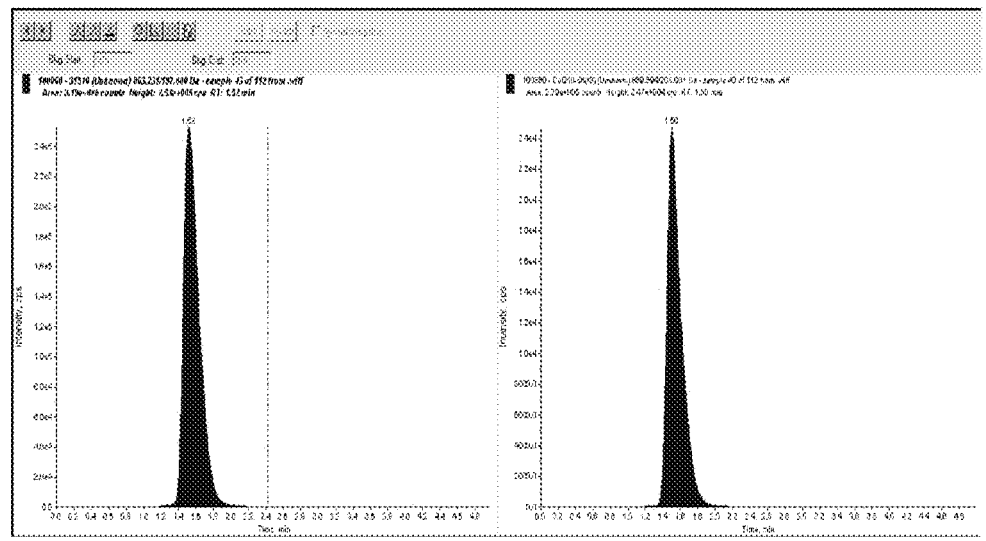

Figure 7. Representative chromatograms for total CoQ10 in cell supernatants.
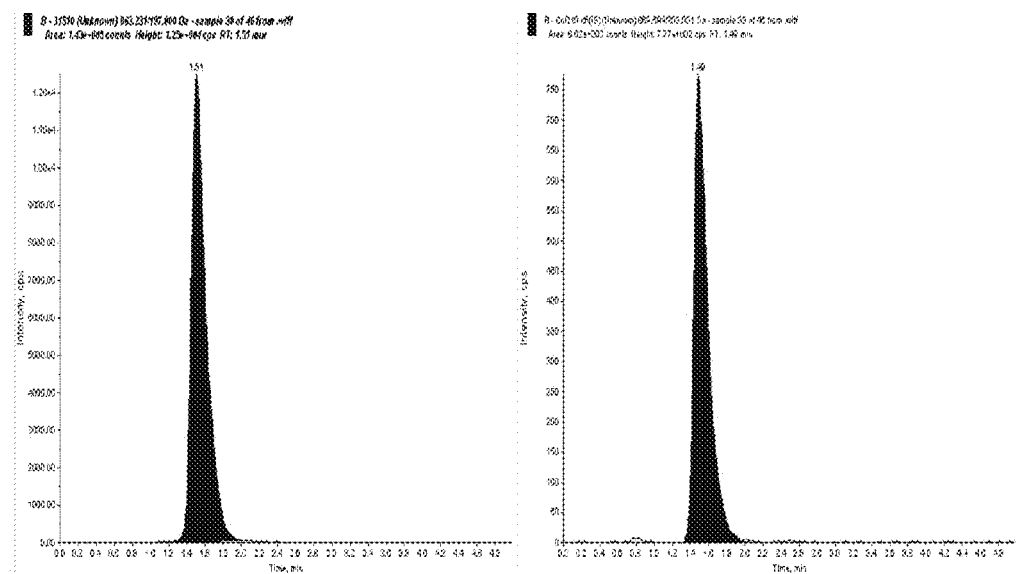

Figure 8. Standard curve and representative chromatograms for total CoQ10 in nasal wash.
Standard Curve
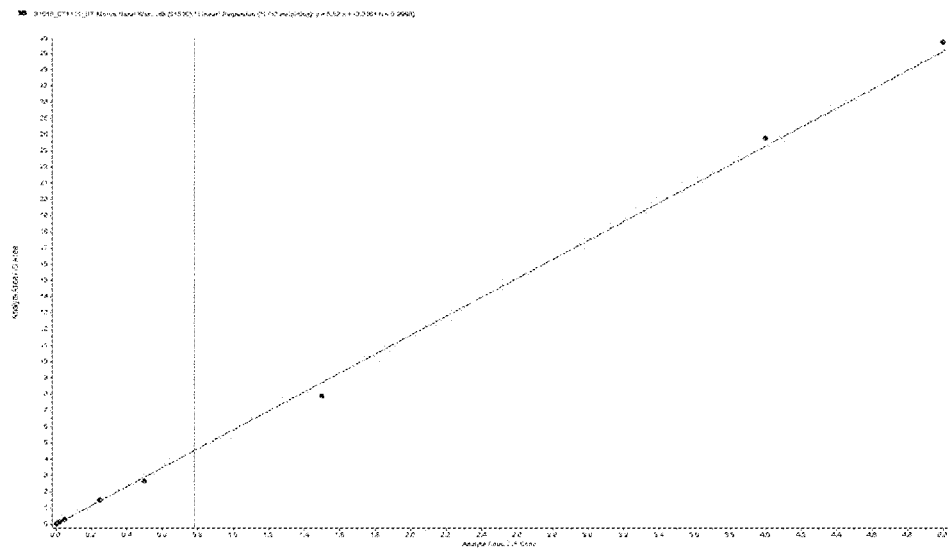
Representative Chromatograms
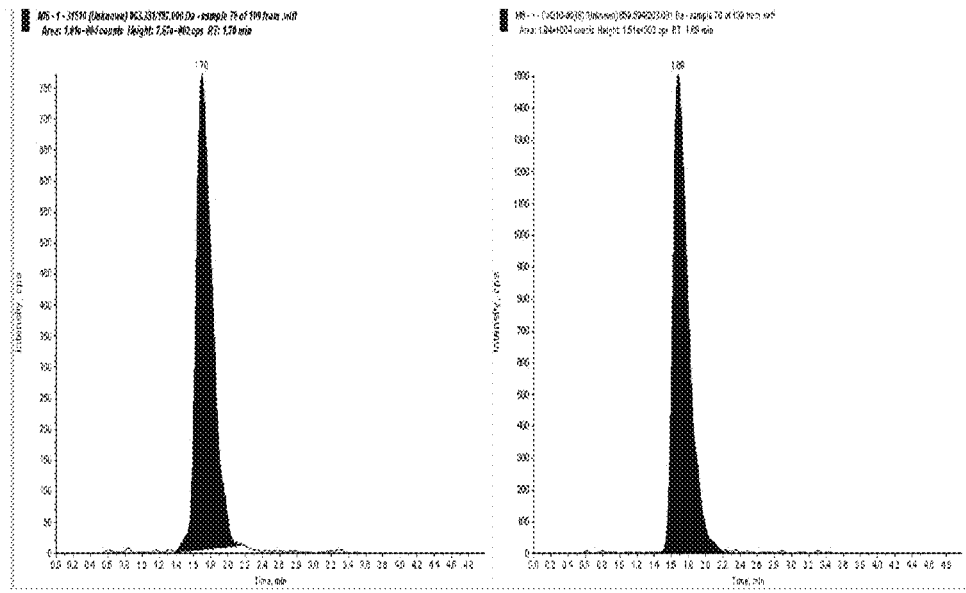

Figure 9. Standard curve and representative chromatograms for total CoQ10 in tissue samples.
Standard Curve
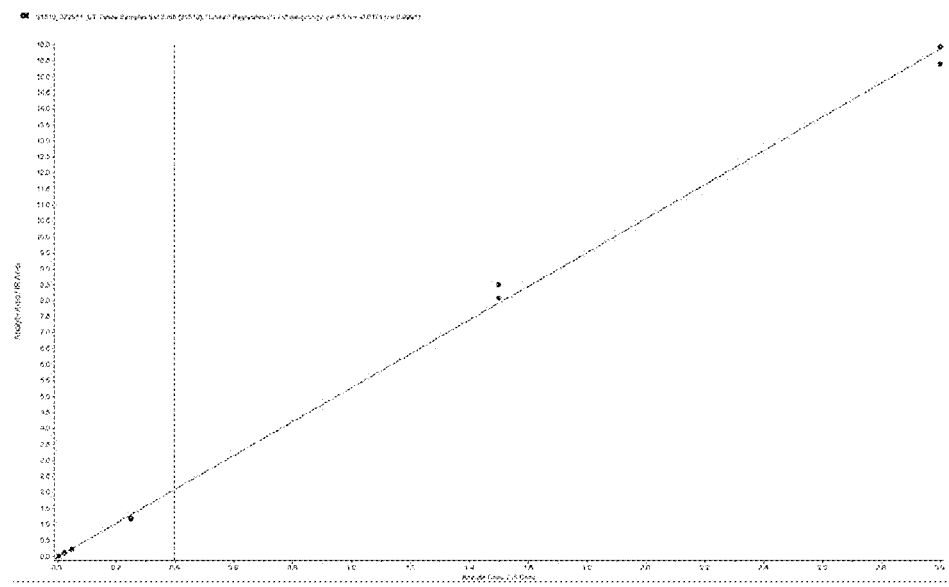
Representative Chromatogram
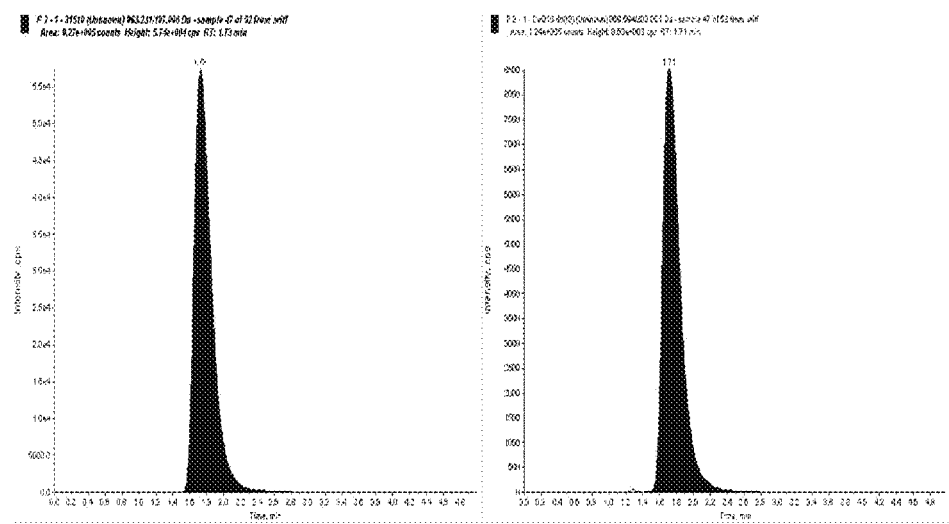

Figure 10. Standard curves for CoQ10- and CoQ10H$_2$ in serum samples.
Standard Curve for Oxidized Form of CoQ10:
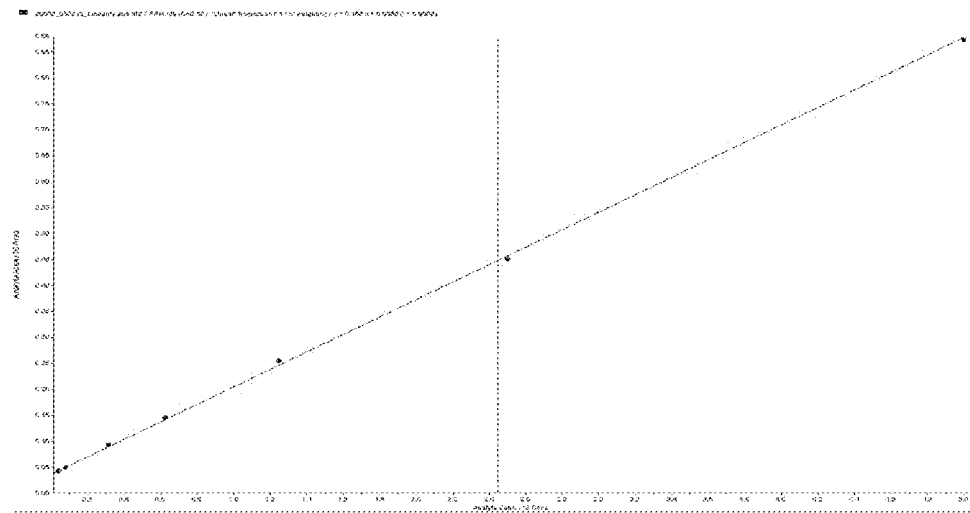
Standard Curve for Reduced Form of CoQ10 (CoQ10H$_2$)
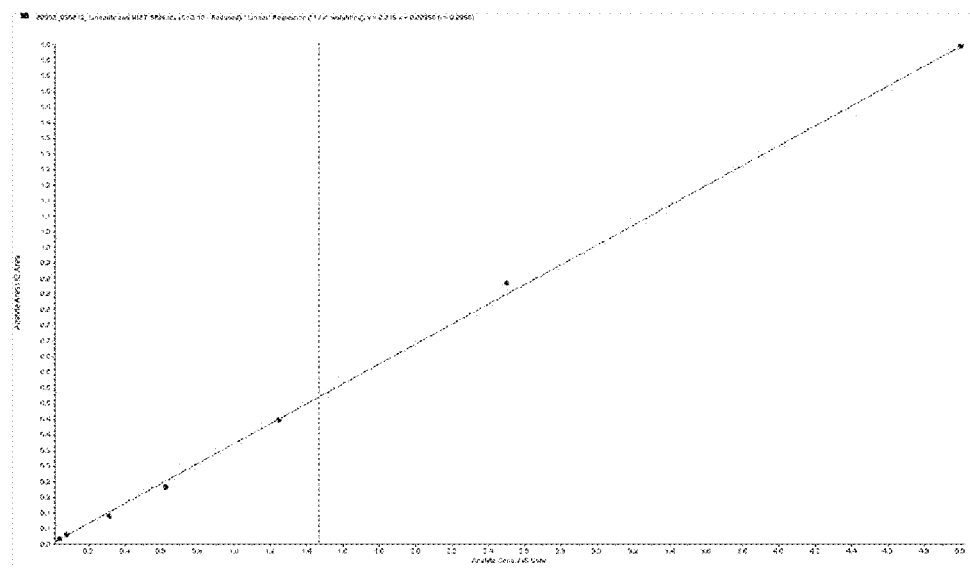

Figure 11. Representative Chromatograms for CoQ10- and CoQ10H$_2$ in serum samples.
Representative Chromatogram for Oxidized Form of CoQ10
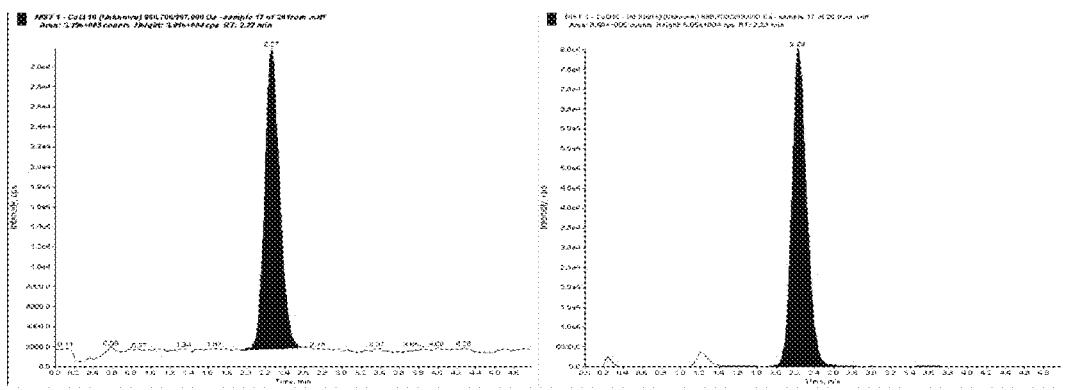
Representative Chromatogram for Reduced Form of CoQ10 (CoQ10H$_2$)
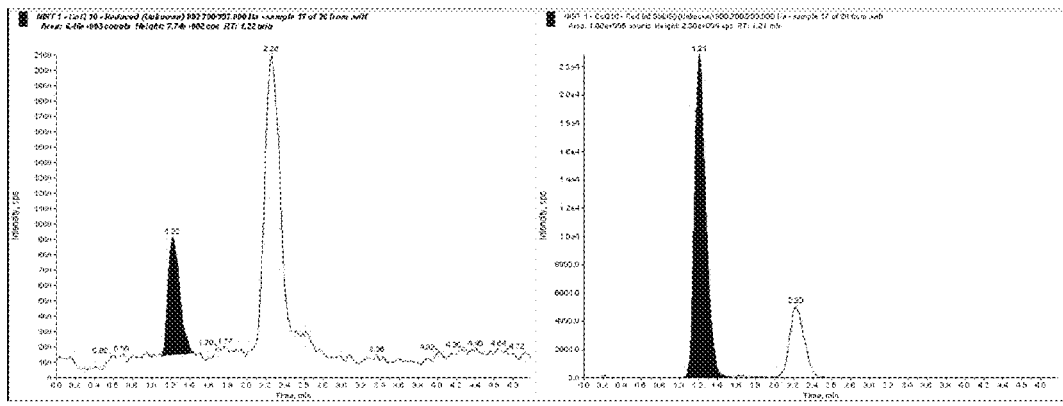

Figure 12. Standard curves for CoQ10- and CoQ10H$_2$ in plasma samples.
Standard Curve for Oxidized Form of CoQ10:
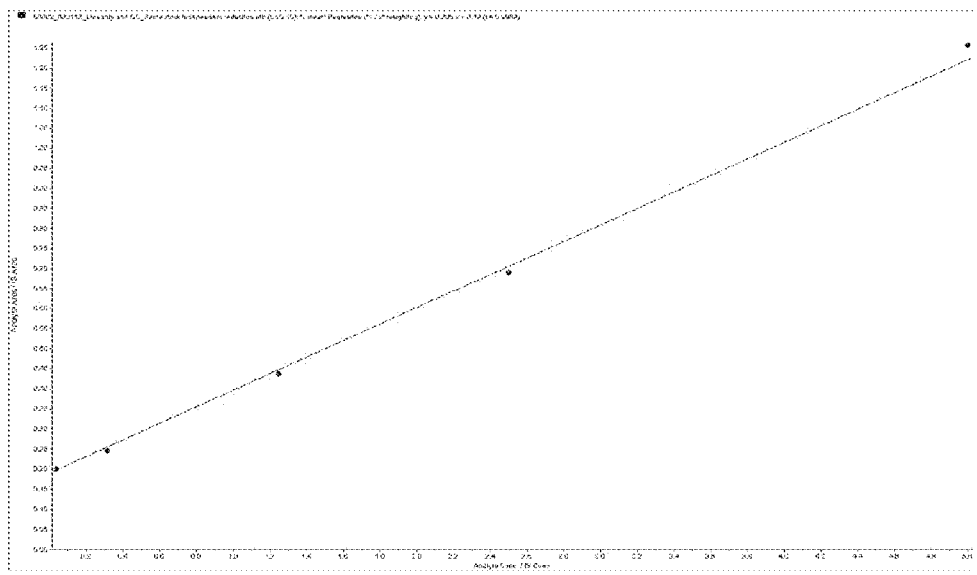
Standard Curve for Reduced Form of CoQ10 (CoQ10H$_2$)
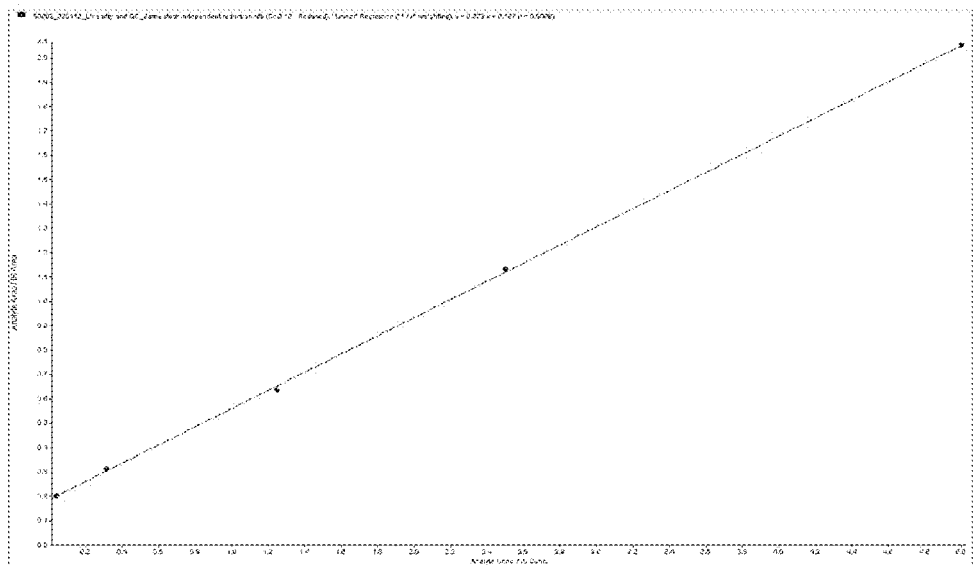

Figure 13. Representative Chromatograms for CoQ10- and CoQ10H$_2$ in serum samples.
Representative Chromatogram for Oxidized Form of CoQ10
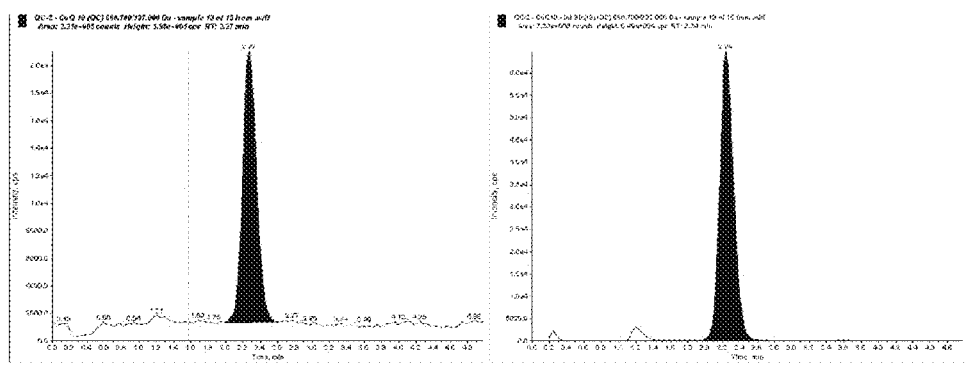
Representative Chromatogram for Reduced Form of CoQ10 (CoQ10H$_2$)
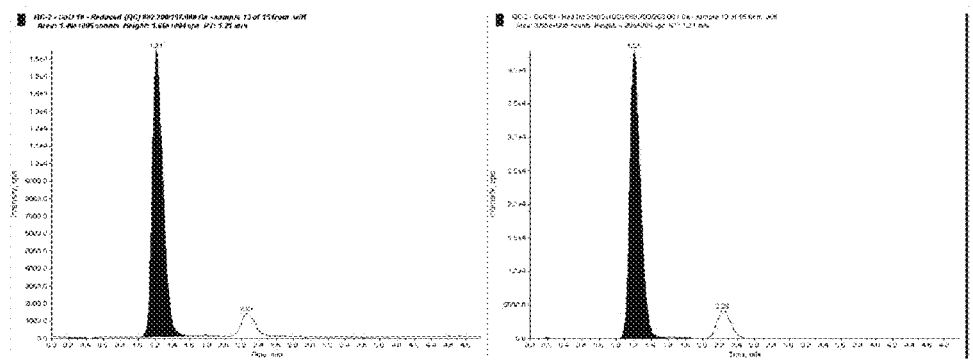

METHODS AND KITS FOR DETECTION OF COENZYME Q10

RELATED APPLICATIONS

This application claims priority to U.S. Provisional Application No. 61/606,019, filed Mar. 2, 2012, the entire contents of which are hereby incorporated herein by reference.

BACKGROUND

Coenzyme Q10, also referred to herein as CoQ10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is found throughout most tissues of the human body and the tissues of other mammals. CoQ10 is very lipophilic and, for the most part, insoluble in water. The insolubility is related to the 50-carbon atom isoprenoid side chain, of hydrocarbon nature as shown in the following structure of CoQ10.

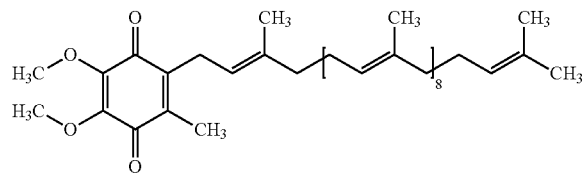

Coenzyme $Q_{10}$ ($CoQ_{10}$) is an integral component of the oxidative phosphorylation machinery in mitochondria and is implicated in homeostasis of biological membranes and cellular redox status. The reduced form of $CoQ_{10}$ ($CoQ_{10}H_2$) is involved in many key physiochemical functions, including serving as an antioxidant, production of ATP, and intercalation with membrane lipids to maintain structure.

SUMMARY OF THE INVENTION

Studies suggest that the lower percentage of $CoQ_{10}H_2$ in total $CoQ_{10}$ (T-CoQ10) is associated with mitochondrial cytopathies, diabetes, heart disease, Parkinson's disease and cancer. Recent studies also suggest that reduced $CoQ_{10}$ levels are associated with an increased risk for prostate cancer in patients taking statins and an increased risk of metastasis in melanoma patients. This underscores the importance of developing methods for robust, accurate, sensitive and specific measurement of $CoQ_{10}$ and $CoQ_{10}H_2$. The invention provides methods for rapid and quantitative extraction and detection of coenzyme Q10 in a sample readily adaptable to high throughput screening methods. The invention further provides reagents and kits for practicing the methods of the invention In one aspect, the invention provides methods for determining the amount of coenzyme Q10 (CoQ10) in a sample by adding a first extraction buffer and a second extraction buffer to the sample that results in phase separation of the sample; and spectroscopically analyzing the second extraction layer to determine the amount of CoQ10.

In another aspect, the invention further provides methods for determining the amount of CoQ10 in a sample by adding a first extraction buffer and a second extraction buffer to the sample; mixing the sample; and analyzing the second extraction layer to determine the amount of CoQ10, wherein a single extraction with the first extraction buffer and the second extraction buffer results in detecting an at least 2-fold greater amount of CoQ10 than using methanol-only extraction.

In another aspect, the invention provides methods for determining the amount of CoQ10 in a sample by adding a first extraction buffer to the sample; heating and mixing the sample; adding a second extraction buffer to the sample that results in phase separation of the sample; heating and mixing the sample; cooling the sample to ambient temperature; and analyzing the second extraction buffer layer to determine the amount of CoQ10 in the sample.

In yet another aspect, the invention provides methods for determining the amount of CoQ10 in a sample by adding a first extraction buffer to the sample; heating and mixing the sample; adding a second extraction buffer to the sample that results in phase separation of the sample; heating and mixing the sample; cooling the sample to ambient temperature; and by performing spectroscopic analysis the second extraction buffer layer to determine the amount of CoQ10 in the sample, wherein a single extraction with the extraction buffer results in extracting at least 2-fold greater amount of CoQ10 than using methanol-only extraction followed by Liquid chromatography/mass spectrometry/mass spectrometry (LC/MS/MS).

In certain embodiments of the invention, the amount of CoQ10 detected in the sample is determined spectroscopically by spectroscopic analysis. In certain embodiments of the invention, the amount of CoQ10 is detected using LC/MS/MS. In certain embodiments of the invention, the amount of CoQ10 extracted using a first extraction buffer and a second extraction buffer is determined spectroscopically, and the amount of CoQ10 detected using methanol-only extraction is determined using LC/MS/MS.

In certain embodiments of the invention, the method is part of a high throughput screening analysis method. In certain embodiments of the invention, the entire method is carried out by automation. In certain embodiments of the invention, the entire method is carried out in a short amount of time. For example, the method is performed using spectroscopic analysis and the amount of CoQ10 in the sample is detected in about half of the time or less, about a quarter of the time or less, or about a tenth of the time or less than would be required to perform the analysis using LC/MS/MS. In certain embodiments, the amount of time to perform analysis on a group of samples using spectroscopic detection methods is compared to the amount of time to perform analysis on a group of samples using LC/MS/MS. In certain embodiments, the amount of time to perform analysis on a group of samples using spectroscopic detection methods is less than 5 hours, less than 4 hours, less than 3 hours, less than 2 hours, less than 30 minutes, less than 15 minutes, less than 10 minutes, less than 5 minutes, less than 4 minutes, less than 3 minutes, less than 2 minutes, less than 1 minutes or less than 30 seconds.

In certain embodiments of the invention, the total amount of CoQ10 detected in the sample, wherein the sample is extracted using a first extraction buffer and a second extraction buffer and the amount of CoQ10 is determined spectroscopically, is at least 2-fold greater than the total amount of CoQ10 detected in a replicate sample using methanol-only extraction followed by LC/MS/MS CoQ10 detection. For example, the total amount of CoQ10 determined spectroscopically, is at least 5-fold, at least 10-fold, at least 15-fold, or at least 25-fold greater than using methanol-only extraction followed by LC/MS/MS CoQ10 detection.

In certain embodiments of the invention, the second extraction buffer comprises a non-polar solvent. In certain embodiments of the invention, the second extraction buffer comprises an organic solvent. In certain embodiments of the invention, the second extraction buffer comprises a solvent selected from the group consisting of benzene, toluene, xylene, hexane, heptane, octane, cyclohexane, 1,4-dioxane, chloroform, diethyl ether, diisopropyl ether, and diisobutyl ether, carbon tetrachloride, dimethyl formamide (DMF), chloromethane, and dichloromethane; or any combination thereof. In certain embodiments of the invention, the second extraction buffer comprise an alkane. In certain embodiments of the invention, the second extraction buffer comprises hexane. In certain embodiments of the invention, the second extraction buffer comprises acetonitrile. In certain embodiments of the invention, the second extraction buffer comprises isopropanol.

In certain embodiments of the invention, the first extraction buffer comprises a polar protic solvent. In certain embodiments of the invention, the first extraction buffer comprises an organic solvent. In certain embodiments of the invention, the first extraction buffer comprises a solvent selected from the group consisting of formic acid, n-butanol, isopropanol, n-propanol, ethanol, methanol, acetic acid, trichloroacetic acid (TCA), and water; or any combination thereof. In certain embodiments of the invention, the solvent comprises an alcohol. In certain embodiments of the invention, the alcohol is methanol.

In certain embodiments of the invention, the first extraction buffer comprises a surfactant.

In certain embodiments of the invention, the first extraction buffer comprises a detergent. In certain embodiments of the invention, the detergent is a mild detergent. In certain embodiments of the invention, the first extraction buffer is an aqueous solution. In certain embodiments of the invention, the first extraction buffer comprises a steroid acid. In certain embodiments of the invention, the steroid acid is a bile acid. In certain embodiments of the invention, the bile acid comprises an acid selected from the group consisting of taurochloric acid, glycocholic acid, cholic acid, chenodeoxycholic acid, deoxycholic acid, and lithocholic acid; or any combination thereof. In certain embodiments of the invention, the bile acid comprises deoxycholic acid. In certain embodiments of the invention, the deoxycholic acid is a salt. In certain embodiments of the invention, the deoxycholic acid salt comprises an inorganic ion that is a group I metal. In certain embodiments of the invention, the inorganic ion of the deoxycholic acid salt comprises an inorganic ion that is a salt selected from the group consisting of $Li^+$, $Na^+$, and $K^+$. In certain embodiments of the invention, the inorganic ion of the deoxycholic acid salt comprises an inorganic ion that is $Na^+$.

In certain embodiments of the invention, the sample comprises a biological sample. In certain embodiments of the invention, the biological sample is a cell based sample. In certain embodiments of the invention, the sample comprises a mammalian sample or amphibian sample. In certain embodiments of the invention, the sample comprises a sample selected from the group consisting of a human sample, a non-human primate sample, and a rodent sample. In certain embodiments of the invention, the sample is a sample from a subject selected from mouse, rat, guinea pig, rabbit, and human.

In certain embodiments of the invention, the spectroscopic analysis is carried out by using a spectroscopic technique selected from absorption spectroscopy, fluorescence X-ray spectroscopy, flame spectroscopy, visible spectroscopy, ultraviolet spectroscopy, infrared spectroscopy, near infrared spectroscopy, Raman spectroscopy, coherent anti-Stokes Raman Spectroscopy (CARS), nuclear magnetic resonance spectroscopy, photoemission spectroscopy, and Mossbauer spectroscopy. In certain embodiments of the invention, the spectroscopic technique is ultraviolet spectroscopy. In certain embodiments of the invention, the ultraviolet spectroscopy is performed at one or more wavelengths of 270 nm to 280 nm. In certain embodiments of the invention, the ultraviolet spectroscopy is performed at one or more wavelengths of 273 nm to 277 nm. In certain embodiments of the invention, the ultraviolet spectroscopy is performed at a wavelength of 275 nm. In certain embodiments of the invention, the ultraviolet spectroscopy is performed at a wavelength between 270 nm and 280 nm, e.g., 270 nm, 271 nm, 272 nm, 273 nm, 274 nm, 275 nm, 276 nm, 277 nm, 278 nm, 279 nm or 280 nm.

In certain embodiments of the invention, the ratio of the volume of the first extraction buffer to the volume of the second extraction buffer is 5:1 to 1:1 (v/v) (e.g., 5:1, 4:1, 3:1, 2:1, or 1:1; or any ranges bracketed by only those values, e.g., 4:1 to 1:1 or 4:1 to 2:1).

In certain embodiments of the invention, the ratio of the surfactant or detergent to the volume of the first extraction buffer is 50:1 to 1:1 (v/v) (e.g., about 45:1, 40:1, 35:1, 30:1, 25:1, 20:1. 15:1, 10:1, 5:1, 2:1, 1:1; or any ranges bracketed by only those values, e.g., 40:1 to 10:1, 40:1 to 5:1, 40:1 to 2:1, 40:1 to 1:1, 35:1 to 10:1, 35:1 to 5:1, 35:1 to 5:1, 35:1 to 1:1, 25:1 to 10:1, 25:1 to 5:1, 20:1 to 5:1, 15:1 to 5:1, 10:1 to 5:1, 10:1 to 2:1, or 10:1 to 1:1).

In certain embodiments of the invention, the sample is heated to 50-100° C., e.g., about 50-100° C., about 55-90° C., about 60-85° C., about 60-80° C., about 55-75° C., about 60-70° C., about 62-68° C., about 63-67° C., about 64-66° C., or about 65° C., after addition of the first extraction buffer, second extraction buffer, or both the first and second extraction buffer. In certain embodiment, the sample is heated to about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In certain embodiments, the sample is heated to the same temperature after addition of the first extraction buffer and the second extraction buffer. In certain embodiments, the sample is heated to different temperatures after addition of the first extraction buffer and the second extraction buffer. In certain embodiments, the sample is heated for a time of at least 5 seconds, at least 10 seconds, at least 15 seconds, at least 20 seconds, at least 30 seconds, at least 40 seconds, at least 50 seconds, at least 60 seconds, at least 75 seconds, at least 90 seconds, at least 105 seconds, or at least 120 seconds, that is less than one, but more than zero, seconds to the upper limit of the range.

In certain embodiments of the invention, the sample is heated for the same amount of time after addition of the first extraction buffer and the second extraction buffer. In certain embodiments, the sample is heated for different amounts of time after addition of the first extraction buffer and the second extraction buffer.

In certain embodiments, heating the sample increases the of extraction of CoQ10 by at least 5%, at least 10%, at least 15%, at least 20%, at least 25%, at least 30%, or at least 50% as compared to a control sample that was not heated.

In certain embodiments of the invention, the sample is mixed by mechanical stirring. In certain embodiments of the invention, the sample is mixed by sonication. In certain embodiments of the invention, the sample is mixed by magnetic stirring. In certain embodiments, the sample is mixed after the addition of the first extraction buffer. In certain embodiments, the sample is mixed after the addition of the second extraction buffer. In certain embodiments, the sample is mixed after the addition of the first extraction buffer and the second extraction buffer.

In certain embodiments of the invention, an inorganic salt is added to the sample after addition of the second extraction buffer. In certain embodiments, the inorganic salt comprises NaCl. In certain embodiments, a saturated brined solution is added to the sample after addition of the second extraction buffer. In certain embodiments, the salt is added to a final concentration of about 1 mM to about 50 mM, that is to a concentration of about 1 mM to about 10 mM, about 1 mM to about 20 mM, about 1 mM to about 30 mM, about 1 mM to about 40 mM, about 5 mM to about 50 mM, about 10 mM to about 40 mM, about 20 mM to about 50 mM, about 10 mM to about 25 mM, about 15 mM to about 35 mM; or any range of values bracketed by only those values, e.g., between about 10 mM to 20 mM.

In certain embodiments of the invention, the sample is filtered prior to spectroscopic analysis of the second extraction buffer.

In certain embodiments of the invention, the entire method is completed within 10 minutes, within 5 minutes, within 1 minute, or within 30 seconds.

The invention provides kits for practicing the method of any of the preceding claims. In certain embodiments, the kit includes at least two of the following: a first extraction buffer, a second extraction buffer. In another aspect, the kit also comprises CoQ10. In a further aspect, the kit comprises a first extraction buffer, a second extraction buffer and instructions for use.

In another aspect, the invention provides, the invention provides novel methods of using oxidized and reduced deuterated internal standard for CoQ10. In certain embodiments, the invention provides an LC-MS/MS method for determining the amount of CoQ10 and $CoQ10H_2$.

In some embodiments, the invention provides a method for determining the amount of coenzyme Q10 (CoQ10) in a sample, the method comprising:
a) adding a known amount of deuterated coenzyme Q10 (CoQ10-d6) to the sample;
b) detecting CoQ10 and CoQ10-d6 by mass spectrometry; and
c) determining the amount of detected CoQ10 by comparing it to the known amount of detected CoQ10-d6.

In some embodiments, the invention also provides a method for determining the amount of reduced form of $CoQ_{10}$ ($CoQ_{10}H_2$) in a sample, the method comprising:
a) adding a known amount of reduced deuterated coenzyme Q10 ($CoQ10H_2$-d6) to the sample;
b) detecting $CoQ10H_2$ and $CoQ10H_2$-d6 by mass spectrometry; and
c) determining the amount of detected $CoQ10H_2$ by comparing it to the known amount of detected $CoQ10H_2$-d6.

In other embodiments, the invention also provides a method for simultaneously determining the amounts of CoQ10 and $CoQ10H_2$ in a sample, the method comprising:
a) adding a known amount of CoQ10-d6 and $CoQ10H_2$-d6 to the sample;
b) detecting CoQ10, $CoQ10H_2$, CoQ10-d6 and $CoQ10H_2$-d6 by mass spectrometry; and
c) determining the amount of detected CoQ10 by comparing it to the known amount of detected $CoQ10H_2$-d6; and
d) determining the amount of detected $CoQ10H_2$ by comparing it to the known amount of detected $CoQ10H_2$-d6.

In still other embodiments, the invention provides a method for determining an extent of $CoQ10H_2$ oxidation in a sample, the method comprising:
a) adding known amounts of $CoQ10H_2$-d6 and/or CoQ10-d6 to the sample;
b) measuring relative amounts of $CoQ10H_2$-d6 and CoQ10-d6 in the sample by mass spectrometry; and
c) comparing theoretical relative amounts of $CoQ10H_2$-d6 and CoQ10-d6 with the relative amounts of $CoQ10H_2$-d6 and CoQ10-d6 measured in step b.

In other aspects, the invention provides a method for determining an extent of $CoQ10H_2$ oxidation in a sample, the method comprising:
a) adding known amounts of $CoQ10H_2$-d6 and/or CoQ10-d6 to the sample;
b) measuring relative amounts of $CoQ10H_2$-d6 and CoQ10-d6 in the sample by mass spectrometry at a first time and a second time
c) comparing theoretical relative amounts of $CoQ10H_2$-d6 and CoQ10-d6 present in the same at the first time with the relative amounts of $CoQ10H_2$-d6 and CoQ10-d6 present in the same the second time;
wherein the change the relative amount of $CoQ10H_2$-d6 and CoQ10-d6 at the first time and the second time is indicative of the extent of oxidation sustained by the sample.

In some embodiments, $CoQ10H_2$-d6 is obtained by reacting CoQ10-d6 with one or more reducing agents. In a specific embodiment, the reducing agent is sodium borohydride.

In some embodiments, CoQ10-d6 and/or $CoQ10H_2$-d6 are added to the sample immediately after sample collection.

In one embodiment, the invention provides a method for determining the amount of CoQ10 in a sample, the method comprising:
a) providing the sample;
b) adding a known amount of CoQ10-d6 to the sample;
c) extracting the sample;
d) optionally subjecting the sample to liquid chromatography;
e) detecting CoQ10 and CoQ10-d6 by mass spectrometry; and
f) determining the amount of detected CoQ10 by comparing it to the known amount of detected CoQ10-d6.

In another embodiment, the invention provides a method for determining the amount of $CoQ10H_2$ in a sample, the method comprising:
a) providing the sample;
b) adding a known amount of $CoQ10H_2$-d6 to the sample;
c) extracting the sample;
d) optionally subjecting the sample to liquid chromatography;
e) detecting $CoQ10H_2$ and $CoQ10H_2$-d6 by mass spectrometry; and
f) determining the amount of detected $CoQ10H_2$ by comparing it to the known amount of detected $CoQ10H_2$-d6.

In yet another embodiment, the invention provides a method for determining the amounts of CoQ10 and $CoQ10H_2$ in a sample, the method comprising:
a) providing the sample;
b) adding known amounts of CoQ10-d6 and $CoQ10H_2$-d6 to the sample;
c) extracting the sample;
d) optionally subjecting the sample to liquid chromatography;
e) detecting CoQ10, CoQ10-d6, $CoQ10H_2$ and $CoQ10H_2$-d6 by mass spectrometry;
f) determining the amount of detected CoQ10 by comparing it to the known amount of detected CoQ10-d6; and
g) determining the amount of detected $CoQ10H_2$ by comparing it to the known amount of detected $CoQ10H_2$-d6.

In some embodiments, step c comprises adding an extraction buffer to the sample, e.g., a first extraction buffer. In a specific embodiment, the extraction buffer, e.g., the first extraction buffer, comprises 1-propanol. In other embodiments, the extraction buffer comprises isopropanol, methanol, ethanol, acetonitrile or acetone. In one embodiment, the extraction with the extraction buffer, e.g., 1-propanol, is followed by a mass spectroscopic analysis of the solvent used for extracton.

In a further embodiment, step c further comprises adding a second extraction buffer that results in phase separation of the sample. In one embodiment, step c comprises:
i. adding a first extraction buffer and a second extraction buffer to the sample;
ii. mixing the sample; and
iii. using the second extraction layer for subsequent steps.

In one embodiment, step c comprises:
i. adding a first extraction buffer to the sample;
ii. heating and mixing the sample;
iii. adding a second extraction buffer to the sample that results in phase separation of the sample;
iv. heating and mixing the sample;
v. cooling the sample to ambient temperature; and
vi. using the second extraction buffer layer for subsequent steps.

In some embodiments, steps b-d are carried out in reduced light. In some embodiments, steps b-d are carried out using pre-cooled solvents. In some embodiments, steps b-d are carried using pre-cooled cryo-block. In some embodiments, the cryo-block is pre-cooled for about 1 hour to about 48 hours, e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 24 hours, about 28 hours, about 32 hours, about 36 hours, about 40 hours, about 44 hours or about 48 hours.

In certain embodiments, the sample is a biological sample. In a specific embodiment, the biological sample is plasma. In another specific embodiment, the biological sample is serum. In another specific embodiment, the biological sample is a tissue. In yet another embodiment, the biological sample is a bodily fluid, e.g., blood, urine, saliva or nasal mucus. In one embodiment, the biological sample is a human sample.

In some embodiment, the invention also provides the kits for carrying out the mass spectrometric methods of the invention. In some embodiment, the kit comprises an extraction buffer, e.g., 1-propanol. In some embodiments, the kit comprises CoQ10-d6. In another embodiment, the kit comprises CoQ10-d6 and one or more reducing agents. In a specific embodiment, the reducing agent is sodium borohydride. In a further embodiment, the kit comprises an extraction buffer, e.g., 1-propanol, CoQ10-d6 and a reducing agent, e.g., sodium borohydride.

Other embodiments are provided infra.

BRIEF DESCRIPTION OF THE DRAWINGS

FIG. 1 shows a representative standard curve of $OD_{275}$ values graphed against the indicated concentrations of CoQ10 in each of acetonitrile, 2-propanol, and hexane. The equations for each line is provided.

FIG. 2 shows a representative standard curve of $OD_{275}$ values graphed against the indicated concentrations of CoQ10 in hexane.

FIG. 3A-E show graphs of representative results of CoQ10 concentrations (pM/cell) in three replicates, and averages, of (A) untreated HepG2 cells; (B) HepG2 cells treated with CoQ10 at 50 μM in propanol; (C) HepG2 cells treated with CoQ10 at 100 μM in propanol; (D) HepG2 cells treated with CoQ10 at 50 μM in a CoQ10 delivery formulation; or (E) HepG2 cells treated with CoQ10 at 100 μM in a CoQ10 delivery formulation; cultured in the presence of CoQ10 for the times indicated and extracted using the methods of the invention.

FIG. 4 shows standard curves for CoQ10- and $CoQ10H_2$, with samples prepared using hexane as a diluent and hexane-reconstituted CoQ10- and $CoQ10H_2$ stocks.

FIG. 5 shows standard curves for CoQ10- and $CoQ10H_2$, with samples prepared using water as a diluent and methanol-reconstituted CoQ10- and $CoQ10H_2$ stocks.

FIG. 6 shows a standard curve and representative chromatograms for total CoQ10 in plasma samples.

FIG. 7 shows representative chromatograms for total CoQ10 in cell supernatants.

FIG. 8 shows a standard curve and representative chromatograms for total CoQ10 in nasal wash.

FIG. 9 shows a standard curve and a representative chromatogram for total CoQ10 in tissue samples.

FIG. 10 shows a standard curves for CoQ10- and $CoQ10H_2$ in serum samples.

FIG. 11 shows representative chromatograms for CoQ10- and $CoQ10H_2$ in serum samples.

FIG. 12 shows a standard curves for CoQ10- and $CoQ10H_2$ in plasma samples.

FIG. 13 shows representative chromatograms for CoQ10- and $CoQ10H_2$ in plasma samples.

DETAILED DESCRIPTION

The present invention relates to methods for rapidly and efficiently extracting CoQ10 from a biological sample, preferably a cell based sample, to detect CoQ10, preferably quantitatively, in the sample. The methods can be readily adapted for use in a high throughput and/automated screening method.

For purposes of optimizing readability and to facilitate understanding of the invention as described herein, it may be beneficial to consider the following definition of terms and phrases as used herein.

I. DEFINITIONS

The detection methods provided herein can be used for the detection of Coenzyme Q10 (CoQ10) and its structural variants. For example, CoQ10 can exist in a fully oxidized form (ubiquinone), a partially oxidized form (ubisemiquinone), and fully reduced form (ubiquinol). Further, although CoQ10 as shown above has 10 isoprenoid units, the methods provided herein can be used for the detection of compounds structurally similar to CoQ10 with about 8-12 (e.g., 8, 9, 10, 11, 12) isoprenoid units, as the ring structure is detected using the spectrophotometric methods preferred herein.

"Total CoQ10", as used herein, refers to the total amount of oxidized and reduced CoQ10 present in a sample.

A "solvent" as used herein is understood typically as a liquid, that dissolves a solid or liquid, resulting in a solution. The solute is soluble in a certain volume of solvent at a specified temperature. As used herein, the solvent does not need to completely solvate all of the sample as long as the non-dissolved components do not interfere with the extraction and detection of CoQ10 in the sample. For example, when whole cell based samples are used, precipitates including proteins and/or nucleic acids can be formed.

Solvents can be subdivided into various groups based on chemical characteristics, solvation/reaction mechanisms, overall charge, charge distribution, etc. For example, solvents can be grouped into non-polar solvents and polar solvents, which can be further subdivided into polar aprotic solvents and polar protic solvents.

The solvents set forth below are ordered by increasing polarity as defined by the dielectric constant. The properties of solvents that are greater than those of water are bolded.

The simplest possible alkane is methane, $CH_4$. There is theoretically no limit to the number of carbon atoms that can be linked together, the only limitation being that the molecule is saturated, and is a hydrocarbon. Saturated oils and waxes are examples of larger alkanes where the number of carbons in the carbon backbone tends to be greater than 10. As used herein, lower alkanes have 1 to 6 carbon atoms. Higher alkanes have at least 7 carbon atoms, preferably 7 to 12

TABLE 1

Organic Solvents

| Solvent | Chemical Formula | Boiling point | Dielectric constant | Density | Dipole moment (D) |
|---|---|---|---|---|---|
| Non-Polar Solvents | | | | | |
| Hexane | $CH_3—CH_2—CH_2—CH_2—CH_2—CH_3$ | 69° C. | 2.0 | 0.655 g/ml | 0.00 D |
| Benzene | $C_6H_6$ | 80° C. | 2.3 | 0.879 g/ml | 0.00 D |
| Toluene | $C_6H_5—CH_3$ | 111° C. | 2.4 | 0.867 g/ml | 0.36 D |
| 1,4-Dioxane | $/—CH_2—CH_2—O—CH_2—CH_2—O—\backslash$ | 101° C. | 2.3 | 1.033 g/ml | 0.45 D |
| Chloroform | $CHCl_3$ | 61° C. | 4.8 | 1.498 g/ml | 1.04 D |
| Diethyl ether | $CH_3CH_2—O—CH_2—CH_3$ | 35° C. | 4.3 | 0.713 g/ml | 1.15 D |
| Polar Aprotic Solvents | | | | | |
| Dichloromethane (DCM) | $CH_2Cl_2$ | 40° C. | 9.1 | 1.3266 g/ml | 1.60 D |
| Tetrahydrofuran (THF) | $/—CH_2—CH_2—O—CH_2—CH_2—\backslash$ | 66° C. | 7.5 | 0.886 g/ml | 1.75 D |
| Ethyl acetate | $CH_3—C(=O)—O—CH_2—CH_3$ | 77° C. | 6.0 | 0.894 g/ml | 1.78 D |
| Acetone | $CH_3—C(=O)—CH_3$ | 56° C. | 21 | 0.786 g/ml | 2.88 D |
| Dimethylformamide (DMF) | $H—C(=O)N(CH_3)_2$ | 153° C. | 38 | 0.944 g/ml | 3.82 D |
| Acetonitrile (MeCN) | $CH_3—C≡N$ | 82° C. | 37 | 0.786 g/ml | 3.92 D |
| Dimethyl sulfoxide (DMSO) | $CH_3—S(=O)—CH_3$ | 189° C. | 47 | 1.092 g/ml | 3.96 D |
| Polar Protic Solvents | | | | | |
| Formic acid | $H—C(=O)OH$ | 101° C. | 58 | 1.21 g/ml | 1.41 D |
| n-Butanol | $CH_3—CH_2—CH_2—CH_2—OH$ | 118° C. | 18 | 0.810 g/ml | 1.63 D |
| Isopropanol (IPA) | $CH_3—CH(—OH)—CH_3$ | 82° C. | 18 | 0.785 g/ml | 1.66 D |
| n-Propanol | $CH_3—CH_2—CH_2—OH$ | 97° C. | 20 | 0.803 g/ml | 1.68 D |
| Ethanol | $CH_3—CH_2—OH$ | 79° C. | 30 | 0.789 g/ml | 1.69 D |
| Methanol | $CH_3—OH$ | 65° C. | 33 | 0.791 g/ml | 1.70 D |
| Acetic acid | $CH_3—C(=O)OH$ | 118° C. | 6.2 | 1.049 g/ml | 1.74 D |
| Water | $H—O—H$ | 100° C. | 80 | 1.000 g/ml | 1.85 D |

"Non-polar solvents" are solvents in which there is (almost) no polarity in the bonds, or, in which the bonds are symmetrically arranged, resulting in balanced pull of charge in all directions. For example, chloroform has relatively strong polar bonds, however, the trigonal planar arrangement of three polar bonds with equal dipole moments makes the molecule non-polar. Alternatively, in alkanes, the bonds have weak dipole moments and almost no polarity in the bonds, making them non-polar. Non-polar solvents include, but are not limited to, alkanes, benzene, toluene, xylenes, hexanes, heptanes, octanes, cyclohexane, 1,4-dioxane, chloroform, diethyl ether, diisopropyl ether, and diisobutyl ether.

Alkanes (also known as paraffins or saturated hydrocarbons) are chemical compounds that consist only of the elements carbon (C) and hydrogen (H) (i.e., hydrocarbons), wherein these atoms are linked together exclusively by single bonds (i.e., they are saturated compounds). Alkanes belong to a homologous series of organic compounds in which the members differ by a constant relative molecular mass of 14. Each carbon atom must have 4 bonds (either C—H or C—C bonds), and each hydrogen atom must be joined to a carbon atom (H—C bonds). As a result, alkanes are typically very stable, and have little biological activity. A series of linked carbon atoms is known as the carbon skeleton or carbon backbone. In general, the number of carbon atoms is often used to define the size of the alkane (e.g., $C_2$-alkane).

carbon atoms. As used herein, middle alkanes have 4 to 8 carbons, or in certain embodiments, 5, 6, or 7 carbon atoms.

Straight-chain alkanes are sometimes indicated by the prefix n- (for normal) where a non-linear isomer exists. Although this is not strictly necessary, the usage is still common in cases where there is an important difference in properties between the straight-chain and branched-chain isomers, e.g., n-hexane or 2- or 3-methylpentane. The members of the series (in terms of number of carbon atoms) are named as follows: methane, $CH_4$— one carbon and four hydrogen; ethane, $C_2H_6$— two carbon and six hydrogen; propane, $C_3H_8$— three carbon and 8 hydrogen; butane, $C_4H_{10}$— four carbon and 10 hydrogen; pentane, $C_5H_{12}$— five carbon and 12 hydrogen; and hexane, $C_6H_{14}$— six carbon and 14 hydrogen. As used herein, unless the n-prefix is used, alkanes are understood to refer to one or more carbon compounds having the indicated number of carbons, and can include mixed populations of the alkane identified (e.g., hexane is understood to include any of n-hexane, 2-methyl pentane, 3-methylpentane, and cyclohexane; and any combination thereof with any ratios of the various hexanes).

"Protic solvents" as used herein, solvate anions strongly via hydrogen bonding. Protic solvents have an acidic hydrogen, although they may be very weak acids. More generally, any molecular solvent which contains dissociable $H^+$, is called a polar protic solvent. The molecules of such solvents can donate an $H^+$ (proton). Protic solvents stabilize ions by stabilizing unshared electron pairs with cations, and by hydrogen bonding with anions.

"Polar protic solvents" favor the SN1 reaction mechanism as the solvents have a hydrogen atom bound to an oxygen, as in a hydroxyl group, or a nitrogen, as in an amine group. Polar protic solvents, as used herein, tend to have high dielectric constants and high polarity. Polar protic solvents include alcohols.

An "alcohol" is any organic compound in which a hydroxyl functional group (—OH) is bound to a carbon atom, in which the carbon atom is usually connected to other carbon or hydrogen atoms. The hydroxyl (OH) functional group in an alcohol molecule, with the dissociable proton in the —OH group, makes the alcohol a polar protic solvent.

Alcohols include, for example, acyclic alcohols have the general formula of $C_nH_{2n+1}OH$ where $n \geq 1$. The suffix -ol appears in the IUPAC chemical name of all substances where the hydroxyl group is the functional group with the highest priority; in substances where a higher priority group is present the prefix hydroxy- will appear in the IUPAC name. The suffix -ol in non-systematic names (such as paracetamol or cholesterol) also typically indicates that the substance includes a hydroxyl functional group and so can be termed an alcohol, but many susbtances (such as citric acid, lactic acid, or sucrose) contain one or more hydroxyl functional groups. As used herein, alcohols can be characterized by the number of carbons present, with lower alcohols having 1-6 carbons (i.e., n=1-6 in the above formula for acyclic alcohols), middle alcohols having 4-8 carbons, and upper alcohols having at least 7 carbons, preferably having 7-12 carbons. Some alcohols include, but are not limited to, methanol ($CH_3OH$), ethanol ($C_2H_5OH$), propanol ($C_3H_7OH$), and pentanol ($C_5H_{11}OH$). As used herein, unless the n-prefix is used, alcohols are understood to refer to one or more carbon compounds having the indicated number of carbons, and can include mixed populations of the alcohol identified.

"Polar aprotic solvents" are solvents that share ion dissolving power with protic solvents but lack an acidic hydrogen. Therefore polar aprotic solvents do not solvate anions, which can inhibit subsequent chemical reactions. These solvents generally have intermediate dielectric constants and polarity. Typically aprotic solvents do not display hydrogen bonding and do not have an acidic hydrogen, but are able to stabilize ions. Nucleophiles are more reactive in aprotic than protic solvents.

"Organic solvents" are solvents that include at least one carbon atom.

"Detergents" as used herein are small amphipathic molecules that tend to form micells in water. Detergents are typically classified according to their hydrophilic/hydrophobic character and ionic groups. Detergents are useful for permeablization/solubilization of membranes, decellularization of organs or tissues, maintaining stability of purified proteins by limiting aggregation, and dissolving lipids and other hydrophobic molecules. Examples of detergents can be found, for example, in 2010 *McCutcheon's Emulsifiers & Detergents* North American edition (McCutcheon's Emulsifiers and Detergents), incorporated herein by reference. A "mild detergent" is typically considered a detergent that does not disrupt the structure of a protein in solution. This allows the determination of the function of the protein. A "mild detergent" typically has a ratio of polar/nonpolar side chain which favors one or the other (e.g. large head group, short aliphatic chain). In general, non-ionic and zwitterionic detergents are more mild than ionic detergents. Of the ionic detergents, bile acids and bile salts are considered to be mild detergents. Anionic detergents are not mild detergents.

Ionic detergents are characterized by their charged hydrophilic headgroups. Ionic detergents can be anionic or cationic. Ionic detergents tend to disrupt both inter- and intramolecular protein-protein interactions. Cationic detergents include, but are not limited to, cationic surfactant solution comprising a selected quaternary amine. The selected quaternary amines are produced through the reaction of a quaternary amine hydroxide and an acid of the group consisting of phosphoric, sulfuric, formic, acetic, propionic, oxalic, malonic, succinic and citric, e.g., an alkyltrimethylammonium or an alkylbenzyldimethylammonium, where the alkyl group contains 12, 14, 16 or 18 carbons. Ionic detergents include deoxycholic acid, sodium dodecyl sulfate (SDS), and hexadecyltrimethylammonium bromide (CTAB).

Non-ionic (or zwitterionic) detergents are characterized by their (net) uncharged, hydrophilic headgroups. They are based on polyoxyethylene glycol (i.e. TWEEN®, TRITON®, and BRIJ® series), CHAPS®, glycosides (i.e. octyl-thio-glucoside, maltosides), bile acids such as deoxycholic acid (DOC), Lipids (HEGAs®), or phosphine oxides (e.g., inorganic phosphorus compounds such as phosphoryl trichloride ($Cl_3P=O$) or organophosphorus compounds with the formula $OPR_3$, where R=alkyl or aryl). Other non-ionic detergents include ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers.

"Surfactants" as used herein, are understood as compounds that lower the surface tension of a liquid, allowing easier spreading, and lowering of the interfacial tension between two liquids, or between a liquid and a solid. Surfactants additionally may act as one or more of detergents, wetting agents, emulsifiers, foaming agents, and dispersants.

The term surfactant is a blend of surface active agent. Surfactants are usually organic compounds that are amphiphilic, meaning they contain both hydrophobic groups (their tails) and hydrophilic groups (their heads). Therefore, a surfactant molecule contains both a water insoluble (or oil soluble component) and a water soluble component. Surfactant molecules migrate to the water surface, where the insoluble hydrophobic group may extend out of the bulk water phase, either into the air or, if water is mixed with an oil, into the oil phase, while the water soluble head group remains in the water phase. This alignment and aggregation of surfactant molecules at the surface acts to alter the surface properties of water at the water/air or water/oil interface.

Bile acids are steroid acids that solvate fats by the formation of micells. Bile acids are useful as both detergents and surfactants. Bile acid refers to the protonated (—COOH) form. Bile salt refers to the deprotonated or ionized (—COO$^-$) form and are typically conjugated to glycine or taurine. Conjugated bile acids are more efficient at emulsifying fats at neutral pH, because they are more ionized than unconjugated bile acids. Bile salts are frequently used as detergents to solvate lipids in protein purification and histochemical methods. Bile salts can also be used as surfactants. Unless otherwise clear from context, as use herein bile acids are understood to include bile acid salts. Bile acids include, but are not limited to, cholic acid, chenodeoxycholic acid, glycholic acid, tauocholic acid, deoxycholic acid, and lithocholic acid. In research deoxycholic acid is used as a detergent for the isolation of membrane associated proteins. Sodium deoxycholate, the sodium salt of deoxycholic acid, is often used as a biological detergent to lyse cells and solubilise cellular and membrane components.

"Critical micellar concentration" or "CMC" refers to both an intrinsic property of amphipathic molecules capable of forming micells, such as surfactants or detergents, and of the amphipathic molecules in solution in the amount of bile acid necessary to function in the spontaneous and dynamic formation of micelles. Upon introduction of surfactants (or any amphipathic molecules capable of forming micells) into the system they initially partition into the interface, reducing the system free energy by a) lowering the energy of the interface (calculated as area×surface tension) and b) by removing the hydrophobic parts of the surfactant from contact with water. Subsequently, when the surface coverage by the surfactants increases and the surface free energy (surface tension) decreases, the surfactants aggregate into micelles, thereby decreasing the system's free energy by decreasing the contact area of hydrophobic parts of the surfactant with water. Upon reaching CMC, any further addition of surfactants will increase the number of micelles. In the methods provided herein, surfactants are typically used at a concentration such that the critical micell concentration is reached in the sample.

As used herein, "salts" are ionic compounds in which the proportions of the ions are such that the electric charges cancel out, so that the bulk compound is electrically neutral. "Inorganic salt" includes salts include, for example, oxides, carbonates, sulfates, and halides. The halides include fluoride ($F^-$), chloride ($Cl^-$), bromide ($Br^-$), iodide ($I^-$) and astatide ($At^-$). Inorganic halide salts include, for example, sodium chloride (NaCl), potassium chloride (KCl), potassium iodide (KI), lithium chloride (LiCl), copper(II) chloride ($CuCl_2$), silver chloride (AgCl), and chlorine fluoride (ClF). As iused herein, a "brined solution" is an inorganic salt solution.

As used herein, a "saturated solution" is understood by its typical definition in physical chemistry as a solution of a substance can dissolve no more of that substance and additional amounts of it will appear as a precipitate. This point of maximum concentration, the saturation point, depends on the temperature of the liquid as well as the chemical nature of the substances involved. As used herein, saturation will be determined at ambient temperature.

As used herein, a "first extraction buffer" includes a polar protic solvent and/or an organic solvent. Polar protic solvents for use in a first extraction buffer include, but are not limited to, alcohols including acyclic alcohols, such as butanol, propanol (i.e., isopropanol and/or n-propanol), ethanol, methanol, hexanol, octanol, etc.; formic acid, acetic acid, and water. As used herein, the first solvent promotes at least one of: disrupting structure of proteins, disrupting cell structure e.g., by creating holes in the cell membrane, promoting at least a limited extraction of proteins, and promoting protein precipitation. As used herein, the first solvent promotes at least two of: disrupting structure of proteins, disrupting cell structure e.g., by creating holes in the cell membrane, promoting at least a limited extraction of proteins, and promoting protein precipitation. As used herein, the first solvent promotes at least three of: disrupting structure of proteins, disrupting cell structure e.g., by creating holes in the cell membrane, promoting at least a limited extraction of proteins, and promoting protein precipitation. As used herein, the first solvent promotes all of: disrupting structure of proteins, disrupting cell structure e.g., by creating holes in the cell membrane, promoting at least a limited extraction of proteins, and promoting protein precipitation. The first extraction buffer is different from the second extraction buffer. In certain embodiments, the first extraction buffer is not methanol.

As used herein, a "second extraction buffer" includes a non polar solvent, for example an organic solvent. The second extraction buffer can include, but is not limited to, benzene, toluene, xylenes, hexane, heptane, octane, hexanes, cyclohexane, 1,4-dioxane, chloroform, diethyl ether, diisopropyl ether, and diisobutyl ether. The second extraction buffer can also include an alkane such as hexane. In certain embodiments, the second extraction buffer is a polar aprotic solvent, such as acetonitrile. As used herein, the second solvent promotes partitioning of CoQ10 away from the first extraction buffer. The second extraction buffer is different from the first extraction buffer.

The term "sample," as used herein, is used in its broadest sense. A "biological sample," as used herein, includes, but is not limited to, any quantity of a substance from a living thing or formerly living thing that can be solubilized in a first extraction buffer optionally containing a surfactant or detergent. Such living things include, but are not limited to, mammals, humans, non-human primates, mice, rats, monkeys, dogs, rabbits, and other animals; plants; single celled organisms such as yeast and bacteria. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes, and spleen, e.g., from resected tissue or biopsy samples; and cells collected, e.g. by centrifugation, from any bodily fluids; and primary and immortalized cells and cell lines. Samples can include fresh samples and historical samples. As used herein, a "cell based sample" is understood as a sample wherein substantially all (e.g., at least 90%, at least 95%, at least 98%, at least 99%) of the CoQ10 present in the sample for detection is present inside cells of the sample (i.e., not in serum, extracellular fluid, cell culture media). In certain embodiments, the methods provided herein are for the detection of CoQ10 in cell based samples.

"Spectrophotometry" or "spectroscopic analysis" as used herein and understood in chemistry is the quantitative measurement of the reflection or transmission properties of a material as a function of wavelength. As used herein, spectrophotometry is related to transmission and detection of visible light, near-ultraviolet, and near-infrared. Preferably, the spectrophotometric methods are used to determine the concentration of a component of a mixture that absorbs light at a particular wavelength, without separating the component to be detected from the other components of the mixture, e.g., by size separation or precipitation. Preferably, the spectrophotometric methods provided herein do not include or require isolation of the CoQ10 from the cell lysate using size based exclusion or separation methods (e.g., chromatography or mass spectrometry) to allow detection of CoQ10 in the sample.

Spectroscopic analysis is selected from absorption spectroscopy, fluorescence X-ray spectroscopy, flame spectroscopy, visible spectroscopy, ultraviolet spectroscopy, infrared spectroscopy, near infrared spectroscopy, Raman spectroscopy, coherent anti-Stokes Raman Spectroscopy (CARS), nuclear magnetic resonance spectroscopy, photoemission spectroscopy, and Mossbauer spectroscopy. CoQ10 is preferably detected at a wavelength near or at 275 nm (e.g., 270-280 nm; 272-278 nm; 274-276 nm), using ultraviolet spectroscopy. In some embodiments, CoQ10 is detected at any wavelength between 270 nm and 280 nm, e.g., 270 nm, 271 nm, 272 nm, 273 nm, 274 nm, 275 nm, 276 nm, 277 nm, 278 nm, 279 nm or 280 nm.

As used herein, "isolation" of CoQ10 as used herein is understood to mean that in the solvent, the CoQ10 is at least 80%, 85%, 90%, 95%, 97%, 98%, or 99% free of materials that naturally occur with CoQ10 (e.g., cellular components, biological sample components).

"Determining the amount" as used herein is performing a step to detect the presence, or absence, of an analyte, e.g., CoQ10, in a sample. In certain embodiments, the amount of analyte determined to be in a sample can be none or below the limit of detection of the method. In certain embodiments, the amount of CoQ10 may be greater than the linear detection range of the method. In such cases, the sample can be diluted in an appropriate buffer prior to spectrophotometric analysis.

The term "control sample," as used herein, refers to any clinically relevant comparative sample, including, for example, a sample from a healthy subject not afflicted with cancer or other disease, a sample from a subject having a less severe or slower progressing cancer or other disease than the subject to be assessed, a sample from a subject having some other type of cancer or disease, a sample from a subject prior to treatment, a sample of non-diseased tissue (e.g., non-tumor tissue), a sample from the same origin and close to the tumor site, and the like. A control sample may include a sample derived from one or more subjects. A control sample may also be a sample made at an earlier time point from the subject to be assessed. For example, the control sample could be a sample taken from the subject to be assessed before the onset of the cancer, or other disease, at an earlier stage of disease, or before the administration of treatment or of a portion of treatment. A control sample can be a purified sample, a chemical compound (e.g., CoQ10), protein, and/or nucleic acid provided with a kit. Such control samples can be diluted, for example, in a dilution series to allow for quantitative measurement of analytes in test samples. The control sample may also be a sample from an animal model, or from a tissue or cell lines derived from the animal model of disease. As the level of CoQ10 varies between tissues, the control can be a tissue specific control. The level of CoQ10 in a control sample that consists of a group of measurements may be determined, e.g., based on any appropriate statistical measure, such as, for example, measures of central tendency including average, median, or modal values.

The term "control level" refers to an accepted or pre-determined level of CoQ10, either a cut-off value, or a series of values used to generate a standard curve, which is used to compare with the spectrophotometric reading used to determine the level of CoQ10 a sample, e.g. a sample derived from a subject. For example, in one embodiment, the control level of CoQ10 is based on the level of CoQ10 in sample(s) from a subject(s) having or suspected of having a particular disease. In another embodiment, the control level of CoQ10 is based on the level in a sample from a subject(s) having a particular rate of disease progression. In another embodiment, the control level of CoQ10 is based on the level of CoQ10 in a sample(s) from an unaffected, i.e., non-diseased, subject(s), i.e., a subject who has not been diagnosed or is not expected to have a particular disease. In yet another embodiment, the control level of CoQ10 is based on the level of CoQ10 in a sample from a subject(s) prior to the administration of a therapy. In another embodiment, the control level of CoQ10 is based on the level of CoQ10 in a sample(s) from a subject(s) having a disease or condition that is not contacted with a test compound. In one embodiment, the control is a standardized control, such as, for example, a control which is predetermined using an average of the levels of CoQ10 from a population of subjects having no particular disease or condition, or diagnosed with a particular disease or condition, or in normal tissue adjacent to abnormal tissue (e.g., normal tissue adjacent to tumor tissue). Control levels can also be ranges, e.g., levels typically detected in normal or control tissues; or control values can include values at the ends of normal ranges, for example, the amount detected relative to the upper level of normal or the lower level of normal.

"Baseline" refers to the level of CoQ10 upon patient entrance into a study or at the initiation of treatment and is used to distinguish from levels of CoQ10 the patient might have during or after treatment. Baseline levels can be used as control levels.

As used herein, "changed as compared to a control" sample or subject is understood as having a level of CoQ10 to be detected at a level that is statistically different than a sample from a normal, untreated, or control sample. Control samples include, for example, cells in culture, particularly untreated or vehicle treated cells, one or more laboratory test animals, or one or more human subjects. Methods to select and test control samples are within the ability of those in the art. An analyte can be a naturally occurring substance that is characteristically expressed or produced by the cell or organism (e.g., CoQ10, an antibody, a protein) or a substance produced by a reporter construct (e.g., β-galactosidase or luciferase). Depending on the method used for detection the amount and measurement of the change can vary. Changed as compared to a control reference sample can also include a change in one or more signs or symptoms associated with or diagnostic of disease, e.g., cancer. Determination of statistical significance is within the ability of those skilled in the art, e.g., the number of standard deviations from the mean that constitute a positive result.

"Mixing" and the like, as used herein, is understood as combining or blending of components, e.g., two or more liquids. Mixing can be continuous or intermittent. Mixing can be performed, for example, by agitation of the container in which the components are contained (i.e., mechanical stirring), by magnetic stirrer, by sonication, by vortexing, or any other method that results in efficient commingling of the components. In preferred embodiments, mixing methods that do not create bubbles that can interfere with later detection methods, particularly in the presence of a surfactant or detergent, are preferred. In certain embodiments, antifoaming agents can be included to reduce or prevent foaming as long as the antifoaming agent does not interfere with detection of CoQ10.

As used herein, "ambient temperature" is understood to be ambient temperature in a laboratory, e.g., typically about 15° C. to about 30° C., preferably about 18° C. to about 25° C. As used herein, cooling to "ambient temperature" is cooling to a temperature that allows for phase separation of the aqueous and organic layers of the treated samples of the invention. Cooling can be performed using a water bath, temperature block, a blower, or other device; or simply by allowing the samples to reach ambient temperature.

As used herein, "heating" the sample is understood as increasing the sample to a temperature of about 50° C. to about 100° C., about 55° C. to about 90° C., 60° C. to about 80° C., about 60° C. to about 70° C., about 62° C. to about 68° C., about 63° C. to about 67° C., or about 65° C.; or a range bracketed by any of the values provided. Heating can be performed using a water bath, temperature block, a blower, incubator, or other device.

Extraction efficiency is determined as the amount of CoQ10 extracted using the methods of the invention relative to the amount of CoQ10 extracted using methanol alone, the method routinely used for CoQ10 extraction prior to detection using mass spectrophotometric methods for CoQ10. In certain embodiments, after extraction, the CoQ10 is detected using spectrophotometry. In certain embodiments, after extraction, the CoQ10 is detected using LC/MS/MS. In certain embodiments, after extraction, the CoQ10 is detected using spectrophotometry for one sample, and LC/MS/MS for the other sample. Extraction efficiency is expressed as increased fold efficiency over extraction methods using methanol alone, e.g., about a 2-, 3-, 4-, 5-, 7-, 10-, 15-, 20-, 25-, 30-, 40-, 50-, 75-, or 100-fold or more increase in efficiency.

As used herein, "automation" is understood as a process carried out by a machine and do not require manual sample or reagent handling. It is understood that some sample and device preparation is required to allow for processing of samples by machine, e.g., determining the appropriate amount of sample for analysis, placing samples in appropriate containers to allow for processing, loading reagents into the machine, programming the machine, and data analysis. As used herein, the process is automated if all of the claimed steps are automated.

As used herein, an isotopically labeled analog of the oxidized form of coenzyme Q10 (CoQ10-d6) is the compound having the following structural formula:

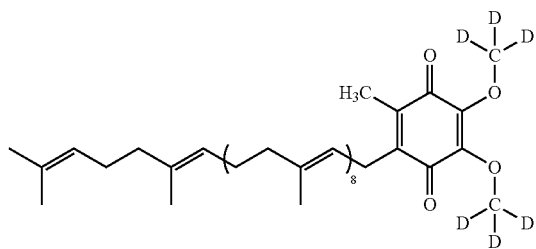

As used herein, an isotopically labeled analog of the reduced form of coenzyme Q10 (CoQ10H$_2$-d6) is the compound having the following structural formula:

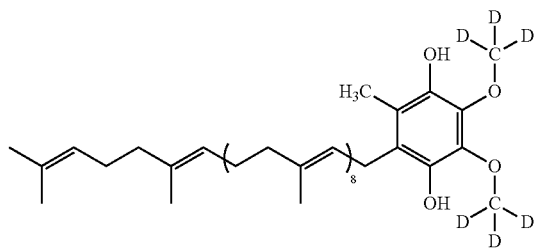

In some embodiments, CoQ10H$_2$-d6 is synthesized by reacting CoQ10-d6 with one or more reducing agents. In some embodiments, the reducing agent is sodium borohydride (NaBH$_4$).

As used herein, "internal standard" is understood as a chemical substance that is added in a known amount directly to each sample containing an analyte. The amount of analyte present is then determined relative to the internal standard as a calibrant.

In some embodiments, the internal standard is an isotopically labeled internal standard, and is an isotopically labeled version of the analyte molecule. The mass spectrometric signal produced by the analyte differs from the mass spectrometric signal produced by the isotopically labeled standard, the difference being dependent on the type and the number of the isotope atoms incorporated into the isotopically labeled version of the analyte. In some embodiments, CoQ10-d6 is an isotopically labeled version of CoQ10 that functions as an internal standard. In some embodiments CoQ10H$_2$-d6 is an isotopically labeled version of CoQ10H$_2$ that functions as an internal standard.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N.sub.2 gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion $M^+$. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form $MH^+$. This tends to occur if M has a high proton affinity. This does not affect quantitation accuracy because the sum of $M^+$ and $MH^+$ is constant. Drug compounds in protic solvents are usually observed as $MH^+$, whereas nonpolar compounds such as naphthalene or testosterone usually form M. See, e.g., Robb et al., Anal. Chem. 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions. As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring" or "multiple reaction monitoring" is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, "amber vial" is a vial made from amber glass. In some embodiments, the amber vial is used to protect the sample contained therein from light.

As used herein, "cryo-block" is a test-tube holder that can keep the test tubes cold for prolonged periods of time.

As used herein, "kits" include two or more reagents to practice the method of the invention in appropriate packaging. For example, a kit can include any one or more of a lysis buffer, a first extraction buffer, a second extraction buffer, and a detergent or surfactant, either in liquid or lyophilized form. In certain embodiments, the kit can include a surfactant and/or CoQ10 for use as a control, e.g., to allow for generation of a standard curve. Kits can also include instructions for performing the methods of the invention.

As used herein, "obtaining" is understood herein as manufacturing, purchasing, or otherwise coming into possession of.

Unless otherwise defined herein, scientific and technical terms used in connection with the present disclosure shall have the meanings that are commonly understood by those of ordinary skill in the art. The meaning and scope of the terms should be clear; however, in the event of any latent ambiguity, definitions provided herein take precedent over any dictionary or extrinsic definition.

Further, unless otherwise required by context, singular terms shall include pluralities and plural terms shall include the singular. "A", "an", and "the" should be understood to include both plural and singular unless stated otherwise or obvious from context. As used herein, "or" should be understood as being inclusive unless stated otherwise or obvious from context.

Also, terms such as "element" or "component" encompass both elements and components comprising one unit and elements and components that comprise more than one subunit unless specifically stated otherwise.

The term "including" and "comprising", and the like, are not limiting and should be understood to allow the inclusion of other components or steps. The term "such as" is used herein to mean, and is used interchangeably, with the phrase "such as but not limited to".

As used herein, "consisting essentially of" and the like is understood to limit the compound, method, or kit to the specified materials or steps "and those that do not materially affect the basic and novel characteristic(s)" of the invention. For example, extraction methods can consist essentially of extraction with a first extraction buffer, a second extraction buffer, a detergent, and optionally a salt with no further extraction or purification steps. However, other steps such as transferring or mixing samples may be included.

Unless otherwise clear from context, all values herein can be understood to be modified by the term "about". The amount of variation tolerated will depend on the specific value, but is typically considered to be within two standard deviations of the mean. "About" can be understood to be a variation of up to 10%, 9%, 8%, 7%, 6%, 5%, 4%, 3%, 2%, 1%, 0.1%, or 0.01%. Ranges provided herein are understood to include all of the values within the range, or any subset of ranges or values within the range. For example, 1-10 is understood to include 1, 2, 3, 4, 5, 6, 7, 8, 9, and 10, or any range or subset of those values, and fractional values when appropriate. Similarly, ranges provided as "up to" a certain value are understood to include values from zero to the top end of the range; and "less than" is understood to include values from that number to zero, e.g., less than 5 is understood as 5, 4, 3, 2, 1, or 0, or a fractional portion of a value within the range of 5 to 0. "One or more than" is understood to include one and all values greater than 1, e.g., 1, 2, 3, 4, 5, 6, 7, 8, etc. or any specific value starting with 1.

"At least a portion" is understood as some fraction (e.g., at least about 1%) of the time, volume, or other entity from which the portion is obtained, to essentially all of (e.g., about 100%) or all of. For example, a sample mixed or heated during an incubation period need not be mixed or heated throughout the entire incubation period. Similarly, typically less than all of the second extraction buffer is analyzed to determine the concentration of CoQ10 in the extracted from the sample.

When ratios of liquids or percent solutions/suspensions of liquids are provided, unless stated otherwise, the ratios are volume to volume. When percent solutions of solids are provided, unless state otherwise, the ratios are weight to volume.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof. When no stereochemistry is provided, all steroisomers, racemic mixtures, or single stereoisomers are included in the term. When both a structure and the name of the structure are provided, in the event of a discrepancy, the structure predominates over the name.

Any embodiment, method, or kit provided herein can be combined with any other embodiment, method, or kit provided herein.

II. METHODS AND USES

Extraction Methods

Provided herein are method and kits for the determination of the amount of CoQ 10 in a biological sample. The extraction methods provided herein can also be used with non-spectrophotometric detection methods, including methods in which the CoQ10 is separated from other components in the sample based on size prior to detection.

The invention provides rapid, efficient methods for the detection of CoQ10 in samples. The methods provided herein can be adapted for automated high throughput screening methods, e.g., for use in clinical laboratories. This is made possible by both the high level of extraction of CoQ10 obtained using the methods provided herein, and by detection of CoQ10 using spectroscopy methods that do not require the isolation of CoQ10 or the detection of CoQ10 based on molecular weight, which allows the method to be adaptable for high throughput screening methods. The extraction methods provided herein can also be used with methods of detection of CoQ10 that include separation of CoQ10 by size, e.g., liquid chromatography, prior to detection. In some embodiments, liquid chromatography is following by mass spectrometric analysis of CoQ10 present in the sample. However, preferred methods of the invention do not include a step for separation of CoQ10 based on the size from other components present in the sample.

In certain embodiments, the methods provided include adding a first extraction buffer and a second extraction buffer to a sample, e.g., a tissue sample or cell sample. The phases then are allowed to separate, and the CoQ10 is retained in the second extraction buffer layer. The second extraction layer is then analyzed spectroscopically to determine the amount of CoQ10 present in the sample.

In certain embodiments, the first and second extraction buffers are added to the sample at the same time (e.g., as an emulsion; sequentially with no predefined incubation time between additions, e.g., within 30 seconds of each other, within 20 seconds of each other, within 10 seconds of each other; with no defined steps, e.g., mixing and/or heating in between). In certain embodiments, the first and second extraction buffers are added to the sample prior to actively mixing the components together, e.g., by mechanically mixing, sonication, or using a magnetic stirrer. In certain embodiments, the sample is incubated with the first extraction buffer prior to addition of the second extraction buffer. In certain embodiments, a surfactant or detergent is added to the sample. In certain embodiments, the surfactant or detergent is mixed with the first extraction buffer prior to addition of the first extraction buffer to the sample. In certain embodiments, the surfactant or detergent is added to the sample at the same time as the first extraction buffer, and optionally at the same time as the second extraction buffer. In certain embodiments, an inorganic salt is added to the sample after the addition of the second extraction buffer. In certain embodiments, the inorganic salt is a chloride salt such as sodium chloride. In certain embodiments, the salt is added as a saturated salt solution, preferably in water. In certain embodiments, the salt would be present at a final concentration of about 1 mM to about 50 mM (e.g., about 5 mM to about 45 mM, about 10 mM to about 35 mM, about 1 mM to about 10 mM, about 1 mM to about 25 mM, about 10 mM to about 50 mM, about 25 mM to about 50 mM, about 20 mM to about 30 mM; about 15 mM to about 35 mM; or any range bracketed by the values provided).

In certain embodiments, the sample is heated during at least a portion of the incubation period with the first extraction buffer, and optionally with the surfactant or detergent, during at least a portion of the incubation period. In certain embodiments, the sample is mixed during at least a portion of the incubation period. In certain embodiments, the sample is mixed and/or heated after the addition of the second extraction buffer. In certain embodiments, the sample is incubated after the addition of both the first and second extraction buffers, and optionally the surfactant or detergent. In certain embodiments, the sample is heated in the presence of the first extraction buffer. In certain embodiments, the sample is heated in the presence of the second extraction buffer. In certain embodiments, the sample is heated in the presence of the first and second extraction buffers. In certain embodiments, the sample is heated in the first buffer, or the second buffer, or in both the first and second buffers for at least 5 seconds, at least 10 seconds, at least 15 seconds, at least 20 seconds, at least 30 seconds, at least 40 seconds, at least 50 seconds, at least 60 seconds, at least 75 seconds, at least 90 seconds, at least 105 seconds, or at least 120 seconds. In certain embodiments, the heating step increases the amount of CoQ10 extracted as compared to a sample not heated during extraction by at least 5%, at least 10%, at least 15%, at least 20%, at least 25%, at least 30%, or at least 50%, or more.

The differences in the physical properties of the first extraction buffer and the second extraction buffer results in spontaneous phase separation of the first and second extraction buffers. In certain embodiments, partitioning can be promoted by cooling a heated sample, either actively or passively, to ambient temperature (i.e., standard laboratory temperature, temperature inside an automated, high throughput assay apparatus). Upon partitioning of the phases, the CoQ10 is present in the second extraction phase, i.e., in the non-polar solvent.

In certain embodiments, after partitioning, at least a portion of the second extraction phase is removed from the sample to facilitate spectroscopic analysis. In certain embodiments, the second extraction phase is removed to a quartz container (e.g., a cuvette, an appropriately shaped tube) for reading at a wavelength of 275 nm to quantitatively detect the presence of CoQ10. The invention provides an advantage over other quantitative methods for the detection of CoQ10 which require the isolation of CoQ10 from substantially all of the other components of the sample to allow for its detection based on size, e.g., using chromatographic methods or mass spectrometry methods which require the separation of molecular species within a mixture, e.g., by separation on a column or electrospray, followed by detection and identification of various components of the species within the mixture. The extraction method provided herein allows for the quantitative detection of CoQ10 in a sample without detecting CoQ10 based on molecular weight. As result, the method is readily adaptable to high throughput methods and can be preformed quickly (e.g., in about 10 minutes or less; in about 5 minutes or less; in about 2 minutes or less; in about 1 minutes or less; in about 30 seconds or less).

The extraction methods provided herein are highly efficient at extracting CoQ10 from sample material, e.g., typically biological material such as cells either grown in culture or from subject samples. Extraction efficiency is determined as the amount of CoQ10 extracted using the methods of the invention relative to the amount of CoQ10 extracted using methanol alone, the method routinely used for CoQ10 extraction prior to detection using liquid chromatograph followed by mass spectrophotometric methods. Extraction efficiency is expressed as the fold increase in efficiency over extraction methods using only methanol, and preferably extraction methods using only methanol followed by liquid chromatography separation, and mass spectrometry detection methods. Using the methods of the invention, extraction is at least, 2-, 3-, 4-, 5-, 7-, 10-, 15-, 20-, 25-, 30-, 40-, 50-, 75-, or 100-fold or more efficient. In certain embodiments, extraction is at least or about 5-, 11-, 14-, 28-, 82-, 545-, or 1863-fold more efficient.

The amount of sample used and the volume of the extraction depend on a number of factors including, but not limited to, the amount of sample available, the volume of the extraction vial and the cuvette for the spectrophotometric analysis. For example, when samples are processed manually, larger volumes are typically used, whereas when automated methods are used, smaller sample volumes may be used.

The ratio of the first extraction buffer to the second extraction buffer is preferably about 5:1 to about 1:1 (v/v) (e.g., 5:1, 4:1, 3:1, 2:1, 1:1, or fractional values within the range bracketed by any of the values, e.g., 4.5:1, 3.3:1, 2.1:1). The ratio of the surfactant or detergent, when present, to the first extraction buffer is preferably about 1:50 to about 1:1 (v/v) (1:50, 1:45. 1:40, 1:35, 1:30, 1:25, 1:20, 1:15; 1:10, 1:5, 1:1). The concentration of the surfactant or detergent is preferably about 0.01 mM to about 10 mM (e.g., about 0.01 mM to about 1 mM, about 1 mM to about 10 mM, about 0.1 mM to about 5 mM, about 0.01 mM to about 2 mM, about 0.1 mM to about 7.5 mM, about 1 mM to about 10 mM, or any range bracketed by any of the values provided). It is understood that some detergents and surfactants are mixed polymers having approximate molecular weights, and therefore only approximate molarities can be provided.

Use of CoQ10-d6 and CoQ10H$_2$-d6 as Internal Standards

Also provided herein are methods of detection and quantification of oxidized and reduced forms of CoQ10 in a sample using mass spectrometry, e.g., LC-MS/MS. The oxidized and reduced forms of CoQ10 in a sample may be detected and quantified separately or they both may be detected and quantified together, in a single analytical run. In a specific embodiment, the methods of the present invention may be used to quantify the amount of reduced CoQ10 (CoQ10H$_2$) present in a sample. These methods allow accurate and reliable quantification of CoQ10H$_2$, which is important because CoQ10H$_2$ is the biologically active form of CoQ10.

In some embodiments, the methods of detection and quantification of oxidized and reduced forms of CoQ10 may be combined with the sample extraction methods described herein or with other extraction methods. For example, in some embodiments, the reduced and oxidized forms of CoQ10 in a sample, e.g., a biological sample, may be detected and quantified by extracting the sample using one extraction buffer, e.g., 1-propanol. In other embodiments, the reduced and oxidized forms of CoQ10 in a sample, e.g., a biological sample, may be detected and quantified by extracting the sample using a first and a second extraction buffer according to the methods described herein.

Quantification of the oxidized and reduced forms of CoQ10 is accomplished by using their respective isotopically labeled versions as internal standards, e.g., oxidized and reduced deuterated COQ10. In some embodiments, CoQ10-d6 is used as an internal standard for determining the amount of CoQ10 in a sample. In some embodiments, CoQ10H$_2$-d6 is used as an internal standard for determining the amount of CoQ10H$_2$ in a sample. In some embodiments, CoQ10-d6 and CoQ10H$_2$-d6 are both added to the sample to be used for simultaneous determination of the amounts of CoQ10 and CoQ10H$_2$ contained in the sample. The amount of CoQ10 in a sample can be calculated based on the known amount of CoQ10-d6 added to the sample and on the relative mass spectrometric signals produced by CoQ10 and CoQ10-d6. Similarly, the amount of CoQ10H$_2$ in a sample can be calculated based on the known amount of CoQ10H$_2$-d6 added to the sample and on the relative mass spectrometric signals produced by CoQ10H$_2$ and CoQ10H$_2$-d6.

The use of CoQ10-d6 as an internal standard for quantifying CoQ10 in a sample, and the use of CoQ10H$_2$-d6 for quantifying CoQ10H$_2$ in a sample provides advantages over the known methods that employ CoQ10-d6 or analogs such as CoQ9 or CoQ11, as internal standards for quantifying both CoQ10 and CoQ10H$_2$. Specifically, the quantification methods described herein provide greater accuracy of CoQ10H$_2$ quantification because CoQ10H$_2$-d6, used in the methods as an internal standard, has properties, e.g., extraction recovery, ionization response and chromatographic retention time that are very similar to those of CoQ10H$_2$, but also produces different mass spectrometric signals. In contrast, the use of CoQ10-d6, CoQ9 or CoQ11 as internal standards for quantifying CoQ10H$_2$ results in a biased quantification and lower accuracy.

The internal standard, e.g., CoQ10-d6 or CoQ10H$_2$-d6, can be added to a sample at any point of the sample work-up procedure. In some embodiments, the internal standard is added to each sample in the beginning of sample processing, e.g., extraction. In some embodiments, the sample comprises blood, and the internal standard is added to the sample prior to plasma extraction.

The amount of internal standard, e.g., CoQ10-d6 or CoQ10H$_2$-d6, to be added to each sample should not interfere with the mass spectrometric signal produced by the analyte, CoQ10 or CoQ10H$_2$. In some embodiments, the amount of CoQ10-d6 or CoQ10H$_2$-d6 to be added to each sample should result in a concentration of CoQ10-d6 or CoQ10H$_2$-d6 that is within the linear range of the dose response curve. In a preferred embodiment, the amount of CoQ10-d6 or CoQ10H$_2$-d6 to be added to each sample should produce a concentration between 20 and 2500 ng/mL, (e.g., 50 and 2000 ng/ml, or 100 and 1500 ng/ml or between 100 and 1000 ng/ml).

In some embodiments, the present invention provides methods for determining the extent of CoQ10H$_2$ degradation that occurs during and as a result of sample processing, e.g., sample extraction. An example of CoQ10H$_2$ degradation is oxidation of CoQ10H$_2$ to produce a partially oxidized form (ubisemiquinone, CoQ10H) or fully oxidized form (ubiquinone, CoQ10). Degradation of CoQ10H$_2$ can be exacerbated by exposure to light and high temperatures that occurs during sample processing and before the sample is introduced into mass spectrometer for detection of CoQ10 and/or CoQ10H$_2$. In some embodiments, the extent of CoQ10H$_2$ oxidation can be calculated based on the known amount of CoQ10H$_2$-d6 added to the sample prior to sample processing and on the measured relative signals of the remaining CoQ10H$_2$-d6 and of CoQ10H-d6 and CoQ10-d6 resulting from oxidation. In a preferred embodiment, the measured amounts of CoQ10 and CoQ10H$_2$ in a sample are adjusted by the amount of CoQ10H$_2$-d6 that becomes oxidized and the amount of CoQ10-d6 that is produced during sample processing.

Methods of CoQ10 and CoQ10H2 Detection Using Mass Spectrometry and Internal Standards In certain embodiments, the invention provides an LC-MS/MS method for determining the amount of CoQ10 and CoQ10H$_2$. This method is linear over the clinically relevant range of 20-2500 ng/mL for both forms, with $r^2>0.99$. The % CV's and inter and intra-assay precision/accuracy values for both forms is below 10%.

In some embodiments, the invention provides methods of determining the amount of CoQ10 and/or CoQ10H$_2$ in a sample, the method comprising:
 a) providing the sample;
 b) optionally adding a known amount of CoQ10-d6 and/or CoQ10H$_2$-d6 to the sample;
 c) processing the sample;
 d) optionally subjecting the sample to liquid chromatography;
 e) detecting CoQ10 and/or CoQ10H$_2$ and, if applicable, CoQ10-d6 and CoQ10H$_2$-d6 by mass spectrometry; and
 f) determining the amount of detected CoQ10 and/or CoQ10H$_2$ in the sample by comparing it to the known amount of detected CoQ10H$_2$-d6.

In some embodiments, the entire method is carried out in reduced light and using amber vials to minimize degradation of CoQ10H$_2$. In some embodiments, the sample collection is carried out using pre-cooled collection tubes to minimize temperature-induced degradation of CoQ10H$_2$. In a further embodiment, the collection tubes may be pre-cooled to a temperature between 0° C. and −20° C. In the preferred embodiment, the collection tubes may be pre-cooled to −20° C. In another embodiment, the collection tubes may be pre-cooled to a temperature of between about −20° C. and −about 80° C., e.g, about −20° C., about −25° C., about −30° C., about −35° C., about −40° C., about −45° C., about −50° C., about −55° C., about −60° C., about −65° C., about −70° C., about −75° C., or about −80° C.

In some embodiments, the sample is blood, e.g., human blood that is collected in pre-cooled BD Vacutainer® Tubes containing Lithium Heparin as the anti-coagulant and processed immediately using standard procedures known in the art that can be used to extract plasma from blood. In a further embodiment, the plasma is separated within 30, preferably, 15 minutes of blood sample collection. In an alternative embodiment, the sample is blood, e.g., human blood that is collected in pre-cooled heparinized vials and kept at low temperature.

In some embodiments, where the blood sample has not been processed within 30 minutes of collection to extract plasma, step c may comprise the extraction of plasma using any plasma extraction method known in the art.

In some embodiments, step c may comprise protein precipitation to remove most of the protein from the sample, leaving CoQ10, CoQ10H$_2$ and their isotopically labeled analogs, if applicable, in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis.

In other embodiments, step c may comprise protein precipitation using extraction with a single solvent. In some embodiments, the solvent for extraction is selected, such that the analyte molecules, e.g., CoQ10 and CoQ10H$_2$, are stable, e.g., not degraded to a significant extent, over a period of time, when placed in the solvent. In some embodiments, the period of time can be up to 6 hours, e.g., 5 minutes, 10 minutes, 30 minutes, 60 minutes, 2 hours, 4 hours or 6 hours. In some embodiments, the solvent may be hexane, methanol, or 1-propanol. In some embodiments, step c is carried out using pre-cooled test tubes, pre-cooled cryo-block and pre-cooled solvents to minimize temperature-induced degradation of CoQ10H$_2$. In a further embodiment, the test tubes, the cryo-block and the solvents may be pre-cooled to a temperature between about 0° C. and about −20° C., e.g., about −2° C. about −5° C., about −10° C., about −12° C., about −15° C., or about −20° C. In the preferred embodiment, the test tubes, the cryo-block and the solvents may be pre-cooled to a temperature of about −20° C. In another embodiment, the test tubes, the cryo-block and the solvents may be pre-cooled to a temperature of between about −20° C. and −about 80° C., e.g, about −20° C., about −25° C., about −30° C., about −35° C., about −40° C., about −45° C., about −50° C., about −55° C., about −60° C., about −65° C., about −70° C., about −75° C., or about −80° C.

In some embodiments, step c may comprise sample extraction using a first extraction buffer and a second extraction buffer, as is described elsewhere in this application.

In some embodiments, the extracted sample may be further subjected to liquid chromatography in step d to separate CoQ10 and CoQ10H$_2$ and their isotopically labeled analogs, if applicable. Traditional chromatographic analysis relies on column packing in which laminar flow of the sample through the column is the basis for separation of the analyte of interest from the sample. The skilled artisan will be able to select LC, including HPLC, instruments and columns that are suitable for use with CoQ10 and CoQ10H$_2$. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. In preferred embodiments, the column is a C18 microparticle packed column (such as Agilent C18 Zorbax column). The chromatographic column includes an inlet port for receiving a sample and an outlet port for discharging an effluent that includes the fractionated sample.

Any chromatographic method that results in effective separation of CoQ10 and CoQ10H$_2$ may be used. In some embodiments, the elution of CoQ10 and CoQ10H$_2$ from a reversed phase column is accomplished using an isocratic elution mode, i.e., wherein the composition of the mobile phase is kept constant. In some embodiments, the composition of mobile phase is 30:70 to 90:10 A:B, wherein A is 5 mM ammonium formate and B is 1-propanol. The composition of the mobile phase can be changed by substituting 5 mM ammonium formate and 1-propanol with any other solvents having similar polarity, including, but not limited to ethanol, 2-propanol, acetone or acetonitrile. In a preferred embodiment, the composition of the mobile phase is 80:20 A:B, wherein A is 5 mM ammonium formate and B is 1-propanol, and the chromatographic separation is carried out for 5 minutes.

In some embodiments, CoQ10 and CoQ10H$_2$ and their isotopically labeled analogs, if applicable, may be detected during chromatography. In some embodiments, the detection may comprise spectroscopic detection. CoQ10 is preferably detected at a wavelength near or at 275 nm (e.g., 270-280 nm; 272-278 nm; 274-276 nm), using ultraviolet spectroscopy.

In preferred embodiments, the eluted CoQ10 and CoQ10H$_2$ and their isotopically labeled analogs, if applicable, are fed directly into a mass spectrometer after chromatographic separation. In an alternative embodiments, the chromatographic fraction comprising the eluted CoQ10 and CoQ10H$_2$ and their isotopically labeled analogs, if applicable, may first be collected and then introduced into a mass spectrometer in a separate step.

In step e, CoQ10 and CoQ10H$_2$ and their isotopically labeled analogs, if applicable, are detected using mass spectrometry. During mass spectrometry, CoQ10 and CoQ10H$_2$ may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

CoQ10 and CoQ10H$_2$ and their isotopically labeled analogs may be ionized in positive or negative mode. In a preferred embodiment, CoQ10 and CoQ10H$_2$ and their isotopically labeled analogs are ionized using ESI in positive ion mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., Rapid Commun. Mass Spectrom. 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). In some embodiments, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of vitamin D metabolites. Methods of generating and using such standard curves are well known in the art and one of ordinary skill is capable of selecting an appropriate internal standard. For example, in preferred embodiments, CoQ10-d6 and CoQ10H$_2$-d6 may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In some embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, CoQ10 and CoQ10H$_2$ in a sample are detected by mass spectrometry using multiple reaction monitoring (MRM) as follows. A sample, e.g., a sample comprising chromatographic fractions of step d and a solvent, enters the nebulizer interface of an MS/MS analyzer and is converted to vapor in the heated charged tubing of the interface. The analyte(s) (CoQ10 and CoQ10H$_2$ and their isotopically labeled analogs, if applicable), contained in the sample, are ionized by applying a large voltage to the solvent/analyte mixture. As the analytes exit the charged tubing of the interface, the solvent/analyte mixture nebulizes and the solvent evaporates, leaving analyte ions. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of derivatized vitamin D metabolites of interest. Precursor ions with the correct mass/charge ratios are allowed to pass into the collision chamber (Q2), while unwanted ions with any other mass/charge ratio collide with the sides of the quadrupole and are eliminated. In some embodiments, the precursor product ion for CoQ10 may be the ion of m/z 863.4, and the precursor product ion for CoQ10H$_2$ may be the ion of m/z 865.4. Using standard methods well known in the art, one of ordinary skill is capable of identifying one or more fragment ions of a particular precursor ion of CoQ10, CoQ10H$_2$, CoQ10-d6 and CoQ10H$_2$-d6 that may be used for further fragmentation in quadrupole 2 (Q2).

Precursor ions entering Q2 collide with neutral argon gas molecules and fragment. The fragment ions generated (i.e., product ions) are passed into quadrupole 3 (Q3), where the fragment ions of analytes are selected while other ions are eliminated. In some embodiments, the product ion of m/z 197 are detected for both CoQ10 and CoQ10H$_2$.

The methods may involve MS/MS performed in either positive or negative ion mode; preferably positive ion mode. Using standard methods well known in the art, one of ordinary skill is capable of identifying one or more fragment ions of a particular precursor ion of CoQ10, CoQ10H$_2$, CoQ10-d6 and CoQ10H$_2$-d6 that may be used for selection in quadrupole 3 (Q3).

As ions collide with the detector they produce a pulse of electrons that are converted to a digital signal. The acquired data is relayed to a computer, which plots counts of the ions collected versus time. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of CoQ10 or CoQ10H$_2$. As described above, the relative abundance of a given ion may be converted into an absolute amount of the original analyte using calibration standard curves based on peaks of one or more ions of an internal standard, e.g., CoQ10-d6 or CoQ10H$_2$-d6.

The following examples are illustrative of the methods of the invention and should not be understood to limit the scope of the invention.

EXAMPLES

Example 1

Materials and Methods

Cell Culture

The assay for quantitation of CoQ10 was used to determine the CoQ10 levels in various cells lines after CoQ10 treatment for various times. The cell lines used in the studies were the normal human aortic smooth muscle cells (HASMC), the hepatic cancer cell line HepG2, and the human pancreatic carcinoma cell line PaCa2. All cells lines are commercially available and were maintained according to instruction from the manufacturer/supplier of the cell lines.

Preparing CoQ10 Standard Solution

A 500 µM CoQ10 stock solution was prepared by weighing 4.32 mg of CoQ10 in a 15 ml conical tube, adding 10 ml of hexane, warming the tube in a water bath at 65° C. until the CoQ10 dissolved, and shaking the tube gently to mix the solution. A 100 µM and 50 µM CoQ10 stock solutions were prepared by diluting the stock solution in hexane.

Reagent Compositions

Buffer A (First extraction buffer): 100% Methanol
Buffer B (Surfactant/detergent): 1 mM Na-deoxycholate
Buffer C (Second extraction Buffer): 100% Hexane General Methods: Extraction/Analysis of a Standard Solution Step 1:

A 500 µM stock solution of CoQ10 was prepared in hexane as described above and used to prepare 100 µM and 50 µM solutions of CoQ10 in the appropriate buffer for cell treatment or for direct use in the detection assay methods.

Step 2:

200 µl of various concentrations of CoQ10 in Buffer A, or Buffer A alone, were aliquoted into glass vials and 10 µl of Buffer B was added to each vial. Cells treated with various concentrations of CoQ10 were collected at predetermined time points and washed. Cell pellet samples (e.g., about $10^5$-$10^7$ cells) were combined with 200 µl of Buffer A and 10 µl of Buffer B, and the cell pellets were resuspended in the buffer mixture. The sample mixture turned opaque upon mixing Buffers A and B with cells. The mixtures were transferred into glass vials.

Step 3:

The glass vials from step 2 were warmed to 65° C. for 1 minute. The samples turned clear upon heating, and again became opaque upon cooling to room temperature.

Step 4:

A 200 µl aliquot of Buffer C was added to each vial. The vials were again warmed to 65° C. The solution in the vials spontaneously partitioned into two phases, with the second extraction buffer layer (upper layer) containing substantially all of the CoQ10 material.

Step 5:

A 50 µl sample of the upper extraction layer was removed and analyzed on a UV spectrometer at 275 nm. The amount of CoQ10 in each sample was determined by comparison to a standard curve.

Example 2

Generation of Standard Curves for CoQ10 Concentrations in Various Solvents

Various solvent systems were tested to optimize the extraction process. To determine optimal spectral properties of the solvent system during analysis using UV spectroscopic detection of CoQ10, standard curves were generated by spectroscopy. Three different solvents (2-propanol, acetonitrile, and hexane) were tested, using known concentrations of CoQ10.

To prepare a standard curve, a 50 µM CoQ10 stock was prepared in the appropriate solvent and serial dilutions of the stock were made. The $OD_{275}$ of each of the samples from the serial dilution was measured at 275 nm in a UV spectrophotometer and plotted on a graph. The results of the standard curve preparation are presented in Table 2 and FIG. 1.

TABLE 2

$OD_{275}$ values for various concentrations of CoQ10 in different solvents

| Concentration of CoQ10 (µM) | Hexane | 2-Propanol | Acetonitrile |
|---|---|---|---|
| 50 | 0.652 | 0.614 | 0.617 |
| 25 | 0.344 | 0.3 | 0.304 |
| 12.5 | 0.166 | 0.154 | 0.145 |
| 6.25 | 0.069 | 0.075 | 0.065 |
| 3.13 | 0.034 | 0.035 | 0.03 |
| 1.56 | 0.016 | 0.016 | 0.012 |
| 0.781 | 0.007 | 0.006 | 0.006 |
| 0.391 | 0.001 | 0.001 | 0 |

A linear regression analysis of the data was performed to generate the standard curves. These results revealed that the spectra of the 2-propanol and acetonitrile solutions were identical, and that the hexane solution deviated slightly in the upper portion of the graph. All three solvents provided results that could be fitted to a linear equation over a substantial range of concentrations Any of the three standard curves could be used to determine the concentration of CoQ10 in the appropriate solvent based on the $OD_{275}$.

Example 3

Quantitation of CoQ10 in Tissue Culture Cells Exposed to Varying Concentrations of CoQ10

Extraction of CoQ10 from Cell Samples

In the experimental trials, about $1 \times 10^6$ HASMC, HepG2, or PaCa2 cells were plated into each well of a 6 well plate. At the time of plating, the cells were treated with defined concentrations of CoQ10, in triplicate, in isopropanol or a proprietary CoQ10 delivery formulation for 3, 6, or 24 hours. After the defined incubation time, the cells were washed with cold TPBS (PBS with 100 mM Tris, pH 7.4), harvested by trypsinization, washed (2×) with 1 ml of TPBS, and pelleted by centrifugation at 1,500 RPM. Immediately after trypsinization, the cells were counted to determine the total number of viable cells in the sample.

Cell pellets were resuspended in 200 µL of Buffer A (first extraction buffer) and 10 µL of Buffer B (surfactant/detergent). Upon addition of Buffer B, the sample became opaque and a precipitate formed. The resuspended cells were transferred to a borosilicate vial. For control samples not containing cells, the CoQ10 containing solution was added to a glass vial and hexane was added to bring the volume to 200 µl, and 10 µl of Buffer B was then added.

The vials were incubated at 65° C. for 2 minutes in a water bath, with gentle mixing at about half way through the incubation. The sample changed from cloudy to clear during the incubation. The sample was removed from the water bath and 200 µL of Buffer C (second extraction buffer) was added to the vial. The sample partitioned into two phases, polar and non-polar. The top, non-polar, layer was clear, while a white precipitate formed the bottom of the vial. The sample was again heated at 65° C. for 1 minute with gentle mixing about half way through the incubation. The solution was cooled to room temperature and a 75 µL aliquot of the upper phase was placed in a quartz cuvette and analyzed by UV spectrophotometry at a wavelength of 275 nm. The absorption was documented.

Generation of Standard Curve

For quantitative assessment of CoQ10 in the biological samples, a standard curve was generated essentially as set forth above (Example 2). For each independent determination of CoQ10, the standard curve was generated by making a 50 µM CoQ10 stock solution in hexane and serially diluting of the stock material. Each of the samples from the serial dilution was measured at a wavelength of 275 nm in a UV spectrometer and plotted on a graph. A representative standard curve is presented in FIG. 2.

A power series was used to fit the standard curve from the standard and an equation was determined. The curve did not fit a typical linear regression form. This lack of linearity demonstrates the benefit of generating a standard curve for each experiment, and the importance of preferably calculating CoQ10 concentrations in unknown samples from $OD_{275}$ readings falling within the linear portion of the curve. Using the $OD_{275}$ values from the extracted samples, the amount of CoQ10 was determined by them against the generated standard curves.

Data Analysis

For this study all cell samples were repeated in triplicate. CoQ10 extractions and $OD_{275}$ measurements were performed by individuals not involved in CoQ10 treatment of the cells or harvesting. As an initial benchmark of the methods used, the data were analyzed for reproducibility.

Hep2G cells not treated with CoQ10, but simply harvested at the indicated times after plating, provided highly reproducible results for all replicate samples (see FIG. 3A). This demonstrates the reproducibility of the extraction and detection methods.

In regard to reproducibility, more variation was seen in cells collected after treatment with various concentrations of CoQ10 for 3, 6, and 24 hours within the triplicate wells. As shown in FIGS. 3B-E, variation in the amount of CoQ10 in Hep 2G cells was observed most substantially at the 24 hour time point.

The results were also analyzed for the efficiency of CoQ10 uptake into cells depending on the delivery vehicle. These results are summarized in Table 3 below. As evident from the data, substantially more CoQ10 was present in cells after 24 when the CoQ10 was delivered in the CoQ10 proprietary delivery formulation than in propanol. The amount of CoQ10 is calculated based on pM of CoQ10 per cell; therefore, the observed difference in intracellular CoQ10 is not a result of a difference in cell viability in response to the two carriers or time to proliferate in culture. Despite the nominal statistical deviations, the data obtained by using the method provided herein were shown to be statistically reliable and the method is reproducible.

TABLE 3

Summary of average levels of CoQ10 in Hep2G cells treated with CoQ10 (pM/cell)

|  | 3 hours | 6 hours | 24 hours |
|---|---|---|---|
| Untreated | 14.63 | 27.40 | 38.07 |
| 50 μM in propanol | 14.40 | 27.07 | 37.04 |
| 100 μM in propanol | 25.20 | 34.74 | 45.43 |
| 50 μM in delivery formulation | 28.1 | 30.2 | 227.57 |
| 100 μM in delivery formulation | 24.7 | 30.2 | 717 |

Example 4

Comparison of the In Vitro Spectrophotometric Method Versus LC/MS/MS (MRM) Method for CoQ10 Quantitation in Biological Samples To further validate the utility of the spectrophotometric method for the quantitative assessment of CoQ10 in biological samples, the experiment described above was repeated using HASMC, HepG2, and PaCa2 cell lines. Further, a second set of cell samples were prepared using each of the three cell types for analysis to determine CoQ10 levels using LC/MS/MS methods routinely used in the art. Briefly, cells were plated and treated with CoQ10 in isopropanol or the CoQ10 proprietary delivery formulation as set forth above, and harvested at 3, 6, or 24 hours after plating. Cell pellets were either extracted using the method set forth above, resuspending the cells in Buffers A and B, and extracting the CoQ10 with Buffer C, or the cell pellets were sent to a diagnostic laboratory (IriSys Research & Development Inc) for quantitative assessment of CoQ10 using extraction with methanol alone followed by LC/MS/MS detection.

The data from the two analyses are summarized in Table 4 below. It is apparent that extraction of CoQ10 from biological samples using methanol alone followed by LC/MS/MS detection resulted in an underestimation of CoQ10 levels in every sample tested and under all treatment conditions when compared to the extraction method described herein followed by spectrophotometric detection. These results demonstrate the efficacy of the extraction and quantitation methods for CoQ10 in biological samples provided herein as compared to techniques that are currently in use. These results also demonstrate more efficient delivery of CoQ10 to cells using the proprietary CoQ10 delivery formulation as compared to isopropanol.

TABLE 4

Comparison of Spectrophotometric and LC/MS/MS Detection of CoQ10

HepG2 Cells

| Sample # | CoQ10 Treatment | Replicate | Formulation | Cells/ml (×10$^5$) | OD$_{275}$ | CoQ10 [μM] | Conc (pM/cell) |
|---|---|---|---|---|---|---|---|
| 1 | Untreated | 1 | Isopropanol | 10.2 | 0.187 | 29.99 | 29.4 |
| 2 | Untreated | 2 | Isopropanol | 7.5 | 0.201 | 32.23 | 42.9 |
| 3 | Untreated | 3 | Isopropanol | 8.03 | 0.21 | 33.67 | 41.9 |
| 4 | Untreated | 1 | Isopropanol | 6.2 | LC/MS/MS | 0.0873 | 0.014 |
| 5 | Untreated | 2 | Isopropanol | 7.1 | LC/MS/MS | 0.0717 | 0.010 |
| 6 | Untreated | 3 | Isopropanol | 8.0 | LC/MS/MS | 0.0788 | 0.010 |
| 7 | 50 μM | 1 | Isopropanol | 13.4 | 0.248 | 39.76 | 29.6 |
| 8 | 50 μM | 2 | Isopropanol | 13.6 | 0.261 | 41.84 | 30.7 |
| 9 | 50 μM | 3 | Isopropanol | 9.9 | 0.321 | 51.45 | 51.9 |
| 10 | 100 μM | 1 | Isopropanol | 5.1 | 0.225 | 36.08 | 70.7 |
| 11 | 100 μM | 2 | Isopropanol | 4.1 | 0.31 | 49.71 | 121.2 |
| 12 | 100 μM | 3 | Isopropanol | 5.0 | 0.315 | 50.51 | 101 |
| 13 | 100 μM | 1 | Isopropanol | 6.1 | LC/MS/MS | 2.061 | 0.34 |
| 14 | 100 μM | 2 | Isopropanol | 5.1 | LC/MS/MS | 1.223 | 0.24 |
| 15 | 100 μM | 3 | Isopropanol | 6.6 | LC/MS/MS | 1.599 | 0.24 |
| 16 | 100 μM | 1 | CoQ10 delivery formulation | 6.8 |  | 53 | 779 |
| 17 | 100 μM | 2 | CoQ10 delivery formulation | 8.3 |  | 65.2 | 785 |
| 18 | 100 μM | 3 | CoQ10 delivery formulation | 11.8 |  | 69.27 | 587 |
| 19 | 100 μM | 1 | CoQ10 delivery formulation | 7.2 | LC/MS/MS | 5.948 | 0.83 |
| 20 | 100 μM | 2 | CoQ10 delivery formulation | 7.7 | LC/MS/MS | 8.864 | 1.15 |
| 21 | 100 μM | 3 | CoQ10 delivery formulation | 1.1 | LC/MS/MS | 6.099 | 0.18 |

TABLE 4-continued

Comparison of Spectrophotometric and LC/MS/MS Detection of CoQ10

| Sample # | Treatment | Replicate | Formulation | Cells/ml (×10⁵) | OD$_{275}$ | CoQ10 [µM] | Conc (pM/cell) |
|---|---|---|---|---|---|---|---|
| HASMC Cells | | | | | | | |
| 22 | Untreated | 1 | Isopropanol | 9.5 | 0.173 | 20.46 | 46.26 |
| 23 | Untreated | 2 | Isopropanol | 1.1 | 0.09 | 10.64 | 95.98 |
| 24 | Untreated | 3 | Isopropanol | 0.3 | 0.051 | 6.02 | 187.87 |
| 25 | Untreated | 1 | Isopropanol | 4.84 | LC/MS/MS | 0.0074 | 0.0015 |
| 26 | Untreated | 2 | Isopropanol | 7.92 | LC/MS/MS | 0.1830 | 0.023 |
| 27 | Untreated | 3 | Isopropanol | 11.4 | LC/MS/MS | 0.0150 | 0.0013 |
| 28 | Untreated | 2 | Isopropanol | 7.7 | LC/MS/MS | 0.0340 | 0.0044 |
| 29 | Untreated | 3 | Isopropanol | 13.5 | LC/MS/MS | 0.0411 | 0.003 |
| PaCa2 Cells | | | | | | | |
| 30 | Untreated | 1 | Isopropanol | 0.61 | 0.057 | 6.79 | 5.51 |
| 31 | Untreated | 2 | Isopropanol | 0.20 | 0.024 | 2.86 | 1.84 |
| 32 | Untreated | 3 | Isopropanol | 1.1 | 0.12 | 14.29 | 9.62 |
| 33 | Untreated | 1 | Isopropanol | 15.0 | LC/MS/MS | 0.021 | 0.0014 |
| 34 | Untreated | 2 | Isopropanol | 14.0 | LC/MS/MS | 0.045 | 0.0032 |
| 35 | Untreated | 3 | Isopropanol | 14.0 | LC/MS/MS | 0.23 | 0.016 |
| 36 | 100 µM | 1 | Isopropanol | 13.2 | 0.239 | 28.46 | 1.56 |
| 37 | 100 µM | 2 | Isopropanol | 13.7 | 0.105 | 12.5 | 9.09 |
| 38 | 100 µM | 3 | Isopropanol | 12.6 | 0.034 | 4.05 | 3.2 |
| 39 | 100 µM | 1 | Isopropanol | 12.0 | LC/MS/MS | 0.371 | 0.31 |
| 40 | 100 µM | 2 | Isopropanol | 11.0 | LC/MS/MS | 1.917 | 0.17 |
| 41 | 100 µM | 3 | Isopropanol | 9.9 | LC/MS/MS | 1.186 | 0.12 |
| 42 | 100 µM | 1 | CoQ10 delivery formulation | 22.0 | 0.17 | 89.23 | 40.56 |
| 43 | 100 µM | 2 | CoQ10 delivery formulation | 23.2 | 0.259 | 135.94 | 58.57 |
| 44 | 100 µM | 3 | CoQ10 delivery formulation | 22.7 | 0.326 | 171.1 | 75.14 |
| 45 | 100 µM | 1 | CoQ10 delivery formulation | 12.0 | LC/MS/MS | 1.501 | 0.12 |
| 46 | 100 µM | 2 | CoQ10 delivery formulation | 11.0 | LC/MS/MS | 4.818 | 0.44 |
| 47 | 100 µM | 3 | CoQ10 delivery formulation | 9.9 | LC/MS/MS | 7.26 | 0.73 |

To facilitate comparison of the amount of CoQ10 detected in the cells, the fold difference of the concentration of CoQ10 per cell detected using the extraction and spectrophotometric methods provided herein was compared to the amount of CoQ10 detected per cell using extraction with methanol only followed by LC/MS/MS detection methods. The results are provided in Table 5 below.

TABLE 5

Fold Difference in CoQ10 Detected in Cells using OD$_{275}$ vs. LC/MS/MS

| Treatment | Cell Type | Formulation | Fold difference |
|---|---|---|---|
| Untreated | HepG2 | Isopropanol | 28 |
| 100 µM | HepG2 | Isopropanol | 82 |
| 100 µM | HepG2 | CoQ10 delivery formulation | 5 |
| Untreated | HASMC | Isopropanol | 545 |
| Untreated | PaCa2 | Isopropanol | 1863 |
| 100 µM | PaCa2 | Isopropanol | 11 |
| 100 µM | PaCa2 | CoQ10 delivery formulaton | 14 |

It can be readily observed that the extraction and detection methods provided herein detect substantially more CoQ10 in a biological sample than the LC/MS/MS methods routinely used in the art.

Example 5

Determination of Mass Spectrometric Parameters for Detection of CoQ10 and CoQ10H$_2$ Oxidized CoQ10 Analysis
Methods:

5.04 mg of CoQ10 was dissolved in 1 mL of acetone for the resulting CoQ10 concentration of 5 mg/mL. A 100 µL aliquot of this solution was mixed with 900 µL of isopropyl alcohol for the resulting CoQ10 concentration of ≈0.5 mg/mL. A 200 µL aliquot of this solution was mixed with 10 µL of formic acid and injected directly into the mass spectrometer. For mass spectrometric analysis, Q1 scan was performed in the positive ESI mode.
Results:

Molecular ion peak for the oxidized form was observed at m/z 863.4. A possible peak for the reduced form of Coenzyme $Q_{10}$ (CoQ10H$_2$) was observed at m/z 885.4. A ghost peak observed at 199.2 Da, which may be caused by previous injections into the mass spectrometer or accumulation of molecules along the internal surfaces.

Product ion scan in the range of 150-800 Da was performed for m/z 863.4 and revealed a single major product ion peat at m/z 197.0.

The peak at m/z 865.4 possibly corresponds to the reduced form of CoQ10 (CoQ10H$_2$). This peak was observed in the Q1 scan but was not as intense as the 863.4 Da peak. A product ion scan performed on this peak revealed m/z 197.0 as the major product peak. This corresponds to the basic ring structure of Coenzyme $Q_{10}$.

A precursor ion scan for m/z 197 was performed and gave 863.9 Da as the major precursor peak. When the m/z range of 850-900 Da was zoomed, a large peak for 863.9, a lower intensity peak for 864.7 Da and a very low intensity peak for 865.8 were observed. These peaks correspond to the completely oxidized (CoQ10) partially reduced (CoQ10H) and completely reduced (CoQ10H$_2$) forms of Coenzyme Q$_{10}$.

Reduced CoQ10 Analysis

Methods:

5.032 mg of CoQ10 was dissolved in 1 mL of hexane to give stock solution of 5 mg/mL stock solution. An aliquot of 100 µL was added to 900 µL of hexane to give the second stock solution at the concentration of 500 µg/mL. 100 µL of the second stock solution was diluted with 1.9 mL of hexane, and then mixed with 50 µL of methanol and 20 mg of sodium borohydride. The reduction reaction was stirred for 3 min and allowed to stand at room temperature in the dark for 5 min. Subsequently, 1 mL water containing 100 mM EDTA was added to the reaction. The final concentration of CoQ10H$_2$ was 25 µg/mL. For mass spectrometric analysis, Q1 scan was performed in the positive ESI mode.

Results:

The Q1 scan for the reduced form of CoQ$_{10}$ did not reveal any molecular ion peak which was consistent and could be related to the structure of the molecule. None of the expected peaks were observed. The possible reason for this may be the addition of EDTA in the last step of the reduction process. EDTA may attach to the molecular ion and form inconsistent adducts, causing irreproducible results.

To remedy inconsistent results caused by EDTA, the above reduction procedure was repeated, but in the last step, 1 mL of water without EDTA was added. The reaction was then mixed with 5 mM ammonium formate in methanol and infused into the mass spectrometer.

Two sets of peaks were observed in this infusion, one set at 863.8, 864.8 and 865.8 m/z and another set at 880.4, 881.3 and 882.4 m/z. These peaks corresponded to the completely oxidized (CoQ10) partially reduced (CoQ10H) and completely reduced (CoQ10H$_2$) forms of Coenzyme Q$_{10}$.

There was also a peak set observed at 880.4, 881.4 and 882.4 m/z that corresponded to the ammoniated adducts of the molecular peaks at 863.8, 864.8 and 865.8 m/z. The product ion scans for all the above peaks revealed 197.0 as the major/only product ion.

The Precursor Ion scan for 197.0 showed peaks for both the above sets of m/z's. The set of peaks formed due to the ammonia adducts showed higher intensity and were used as precursor ions for finalizing mass spectrometer parameters.

Example 6

Determination of Chromatographic Parameters for Detection of CoQ10 and CoQ10H$_2$ Methods:

1 mg of CoQ10 was dissolved in 1 mL of Hexane, and 100 µL of this solution was added to 900 µL of hexane, resulting in a 100 µg/mL stock solution.

For the reduction reaction, 100 µL of stock solution was diluted with 1.9 mL of hexane and mixed with 50 µL of methanol and 20 mg of sodium borohydride. The reaction was stirred for 3 min and stored at room temperature in the dark for 5 min. Complete conversion of the oxidized to reduced form was confirmed visually by the change of reaction color from yellow to colorless. Subsequently, 1 mL of water was added and mixed. The reaction was centrifuged at 13,000 rpm for 2 min to separate the layers. The top hexane layer containing CoQ10H$_2$ at the concentration of 5 µg/mL was collected (CoQ10H$_2$ stock).

The above reaction was repeated in another tube without the addition of sodium borohydride. The top hexane layer containing CoQ10 at the concentration of 5 µg/mL was collected (CoQ10 stock).

Liquid chromatography was performed using 10 mM ammonium formate in methanol as mobile phase A, 1-propanol as mobile phase B and the C18 Zorbax column. The stocks containing CoQ10 and CoQ10H$_2$ were mixed at the 1:1 ratio and injected into the chromatograph. Three isocratic 5 minute runs were performed using the mobile phase where A and B were mixed at the ratios of 20:80; 50:50; 80:20. The ratio if 80:20 resulted in the best separation of CoQ10 and CoQ10H2 peaks.

Example 7

Standard Curves

TABLE 6

Preparation of samples for standard curve

| Label | Stock Used | Vol of stock | Diluent | Vol Diluent | Conc (ng/mL) |
|---|---|---|---|---|---|
| L8 | 1:1 OXD:RED | 1 mL | Hexane | 0 | 2500 |
| L7 | L8 | 500 µL | Hexane | 500 µL | 1250 |
| L6 | L7 | 500 µL | Hexane | 500 µL | 625 |
| L5 | L6 | 500 µL | Hexane | 500 µL | 323 |
| L4 | L5 | 500 µL | Hexane | 500 µL | 157 |
| L3 | L4 | 500 µL | Hexane | 500 µL | 79 |
| L2 | L3 | 500 µL | Hexane | 500 µL | 39 |
| L1 | L2 | 500 µL | Hexane | 500 µL | 19 |

The samples were separated by liquid chromatography using methods described in the Example 6 with mobile phase A:B 80:20. Shown in FIG. 4 are standard curves obtained for CoQ10 and CoQ10H$_2$.

When samples for the standard curve were prepared using HPLC grade water as a diluent instead of hexane, with the same LC-MS/MS conditions, and were used for the run, no detectable area counts were seen at any of the concentrations for the reduced and the oxidized forms of CoQ$_{10}$.

The above experiment was repeated using different extraction solvents in an attempt to extract CoQ$_{10}$ from water. The extraction solvents tested were 100% isopropyl alcohol, 100% Hexane, and 20:80 Ethanol:Hexane. Three sets of samples for standard curves were extracted using each extraction solvent. It was observed that the area recoveries within all samples extracted with the same extraction solvent were similar, but the area recoveries differed for each extraction solvent group None of the extraction solvents gave a linear relationship between area counts and spiked concentration. It was ascertained that HPLC grade water did not uniformly homogenize with the standards in hexane, probably due to water's high polarity.

To tackle the problem of immiscibility of hexane and water, the CoQ10 and CoQ10H$_2$ stocks in hexane were evaporated under a gentle stream of nitrogen and reconstituted in methanol. These reconstituted standards were then used to prepare samples for the standard curve with HPLC water as a diluent, and the standards were analyzed using the above LC-MS/MS procedure. These samples gave a linear curve for the area responses when plotted against concentration, as is shown in FIG. 6.

CoQ10-d6 internal standard was also reduced using the same procedure as described above. When a serial dilution of the internal standards were made, with hexane evaporated and reconstituted in methanol, similar linear relationship was observed.

CoQ10 and CoQ10H$_2$ stocks in hexane were evaporated and reconstituted in methanol. CoQ10-d6 and CoQ10H$_2$-d6 stocks in hexane were also evaporated and reconstituted in methanol. These reconstituted standards were then used to prepare samples for the standard curve with HPLC water as a diluent. 100 μL of each sample was aliquoted into new tubes and extracted using three different extraction solvents described above. The area responses for all concentrations within the same extraction solvent group were found to be similar, with no linear relationship between area response and concentrations fortified.

CoQ10, CoQ10H$_2$, CoQ10-d6 and CoQ10H$_2$-d6 stocks in hexane were evaporated and reconstituted in methanol. The reconstituted standards were then used to prepare samples for the standard curve with plasma as a diluent to give a linear concentration range of 19-2500 ng/ml of CoQ10 and CoQ10H$_2$. 20 μL of 25 μg/mL of CoQ10-d6 and CoQ10H$_2$-d6 s was added to each tube. Subsequently, each sample was extracted using 1 mL of ethanol:hexane 20:80. Each sample was vortexed vigorously for 4-5 min, centrifuged and 150 μL of the top layer was removed and put it into LC-MS/MS vials for analysis. All of the above steps were carried out as quickly as possible using a cryo-block cooled to −20° C., and 10 μL from each tube was injected for LC-MS/MS analysis.

A linear relationship was observed between the area ratios and concentrations spiked. Due to the high concentrations of the oxidized and reduced forms, there was overlap between the peaks and hence no baseline separation was observed.

In the next experiment, 50 μL of the standards was used as the starting point and 1.5 mL of the extracting solvent was used. Different injection volumes were tried. Injecting 3 μL of the standards gave a baseline separated chromatogram with linear response and r$^2$ values of ≥0.99.

Example 8

Quantification of Total CoQ10 in Plasma Samples

In this experiment, the amount of total CoQ10 in different plasma samples was measured. A single isopropanol extraction of each plasma sample was used to extract CoQ10, which was subsequently quantified using LC-MS/MS. The standard curve, shown in the graph in FIG. 6, was constructed using the samples containing 0, 3, 5, 10, 50, 100, 300, 500, 800 and 1000 μg/mL of CoQ10, analyzed in duplicates. The calculated % accuracy for the measurements of CoQ10 concentration in the samples used for the standard curve ranged from 91.3% to 113% for samples with CoQ10 concentration ranging between 5 and 800 μg/mL. The results of the analyses of plasma samples, each containing unknown amount of CoQ10 is presented in the table 7 below.

TABLE 7

CoQ10 in plasma samples

| Sample Name | Analyte Peak Area (counts) | Area Ratio | IS Peak Area (count) | Calculated Concentration (μg/mL) |
|---|---|---|---|---|
| Solvent (isopropanol) | 1.11 × 10$^2$ | 4.54 | 24.4 | N/A |
| Blank plasma | 64.1 | 29.1 | 22.1 | N/A |

TABLE 7-continued

CoQ10 in plasma samples

| Sample Name | Analyte Peak Area (counts) | Area Ratio | IS Peak Area (count) | Calculated Concentration (μg/mL) |
|---|---|---|---|---|
| Blank plasma | 0 | 0 | 73.2 | N/A |
| Unknown Sample 1 | 7.79 × 10$^3$ | 2.62 × 10$^2$ | 2.97 × 10$^5$ | 3.07 |
| Unknown Sample 2 | 6.95 × 10$^5$ | 2.16 | 3.21 × 10$^5$ | 299 |
| Unknown Sample 3 | 1.13 × 10$^6$ | 3.75 | 3.00 × 10$^5$ | 520 |
| Unknown Sample 4 | 2.19 × 10$^6$ | 7.31 | 3.00 × 10$^5$ | 1010 |
| Unknown Sample 5 | 3.19 × 10$^6$ | 11.4 | 2.97 × 10$^5$ | 1580 |

Example 9

Quantification of Total CoQ10 in Cell Supernatants

This experiment was designed to assess the uptake of CoQ10 by cultured cells after they have been exposed to formulations containing CoQ10. Caco-2 cells were cultured according to known protocols and were exposed to CoQ10 containing formulations for 0, 1, 2, 3, 4 and 6 hours. After a wash and lysis, the cell lysate was extracted with isopropanol, and the amount of CoQ10 in the extract was measured by LC/MS. The standard curve, shown in the graph in FIG. 7, was constructed using the samples containing 0, 0.01, 0.05, 0.1, 0.5, 1, 3, 5, 7 and 10 μg/mL of CoQ10. The calculated % accuracy for the measurements of CoQ10 concentration in the samples used for the standard curve ranged from 87.6% to 107% for samples with CoQ10 concentration ranging between 0.5 and 10 μg/mL. The results of the analyses of spiked cell culture media (Unknown Samples A-H) and cell supernatants (unknown Samples I-L) are presented in the table below.

TABLE 8

CoQ10 in cultured cell lysates

| Sample Name | Analyte Peak Area (counts) | Area Ratio | IS Peak Area (count) | Calculated Concentration (μg/mL) |
|---|---|---|---|---|
| Solvent (isopropanol) | 15.3 | 44.4 | 0.346 | N/A |
| Unknown Sample A | 2.84 × 10$^5$ | 33.5 | 8.47 × 10$^3$ | 3.93 |
| Unknown Sample B | 1.43 × 10$^5$ | 16.5 | 8.62 × 10$^3$ | 2.11 |
| Unknown Sample C | 7.32 × 10$^4$ | 85.3 | 8.58 × 10$^3$ | 1.14 |
| Unknown Sample D | 3.30 × 10$^5$ | 43.4 | 7.62 × 10$^3$ | 4.88 |
| Unknown Sample E | 1.67 × 10$^5$ | 19.3 | 8.66 × 10$^3$ | 2.43 |
| Unknown Sample F | 7.89 × 10$^4$ | 9.7 | 8.13 × 10$^3$ | 1.29 |
| Unknown Sample G | 4.22 × 10$^4$ | 4.93 | 8.57 × 10$^3$ | 0.679 |
| Unknown Sample H | 0 | 0 | 8.35 × 10$^3$ | No Peak |
| Unknown Sample I | 8.27 × 10$^5$ | 131 | 6.29 × 10$^3$ | 11.5 |
| Unknown Sample J | 1.23 × 10$^4$ | 1.28 | 9.56 × 10$^3$ | 0.187 |
| Unknown Sample K | 8.11 × 10$^5$ | 131 | 6.21 × 10$^3$ | 11.5 |
| Unknown Sample L | 1.82 × 10$^4$ | 2.07 | 8.80 × 10$^3$ | 0.295 |

Example 10

Quantification of Total CoQ10 in Nasal Wash

This experiment was designed to assess the uptake of CoQ10 by the mucous membranes in the nasal cavity after administration of the proprietary nasal formulation of CoQ10. After intranasal administration of the proprietary formulation to rats, the mucus and liquid from rats' nasal cavity was collected after 30 minutes and 1 hour, extracted with isopropanol, and the amount of CoQ10 in the extract was measured by LC-MS/MS. The standard curve, shown in the graph in FIG. 8, was constructed using the samples containing 0, 1, 5, 10, 50, 100, 300, 800 and 1000 µg/mL of CoQ10. The calculated % accuracy for the measurements of CoQ10 concentration in the samples used for the standard curve ranged from 90.5% to 114% for all standard samples. The results of the analyses of cell extracts is presented in the table below, where M1, M2, M3, M4 and M5 refer to different individual rats.

TABLE 9

CoQ10 in nasal wash

| Sample Name | Time of Exposure to Nasal Formulation | Analyte Peak Area (counts) | Area Ratio | IS Peak Area (count) | Calculated Concentration (µg/mL) |
|---|---|---|---|---|---|
| Solvent (isopropanol) | N/A | $2.07 \times 10^2$ | 12.3 | $1.68 \times 10^1$ | N/A |
| M1 | 30 minutes | $1.02 \times 10^3$ | $4.85 \times 10^{-2}$ | $2.10 \times 10^4$ | 2.22 |
| M1 | 1 hour | $2.19 \times 10^3$ | $1.05 \times 10^{-1}$ | $2.09 \times 10^4$ | 4.15 |
| M2 | 30 minutes | $1.57 \times 10^3$ | $7.66 \times 10^{-2}$ | $2.05 \times 10^4$ | 3.18 |
| M2 | 1 hour | $2.34 \times 10^3$ | $1.20 \times 10^{-1}$ | $1.95 \times 10^4$ | 4.68 |
| M3 | 30 minutes | $1.70 \times 10^3$ | $9.09 \times 10^{-2}$ | $1.87 \times 10^4$ | 3.68 |
| M3 | 1 hour | $1.09 \times 10^3$ | $5.68 \times 10^{-2}$ | $1.92 \times 10^4$ | 2.5 |
| M4 | 30 minutes | $5.21 \times 10^3$ | $2.83 \times 10^{-1}$ | $1.84 \times 10^4$ | 10.3 |
| M4 | 1 hour | $1.04 \times 10^3$ | $5.15 \times 10^{-2}$ | $2.02 \times 10^4$ | 2.32 |
| M5 | 30 minutes | $3.16 \times 10^3$ | $1.60 \times 10^{-1}$ | $1.97 \times 10^4$ | 6.06 |

Example 11

Quantification of Total CoQ10 in Tissues

This experiment was designed to determine the amount of CoQ10 present in different tissues of mice that have been administered a proprietary CoQ10 formulation. After administration, the mice were sacrificed after 0.5, 1, 3, 8, 24 or 48 hours. The lungs, liver and kidneys were homogenized, and the homogenate was extracted with isopropanol. The amount of CoQ10 in the extract was measured by LC-MS/MS. The standard curve, shown in the graph in FIG. 9, was constructed using the samples containing 1, 5, 10, 50, 100, 300, and 600 µg/mL of CoQ10. The calculated % accuracy for the measurements of CoQ10 concentration in the samples used for the standard curve ranged from 90.2% to 121% for all standard samples. The results of the analyses of tissue extracts is presented in the table below, where P1 and P2 refer to two individual mice.

TABLE 10

CoQ10 in tissues

| Sample Name | Time of Exposure to Formulation (hours) | Analyte Peak Area (counts) | Area Ratio | IS Peak Area (count) | Calculated Concentration (µg/mL) |
|---|---|---|---|---|---|
| Solvent (isopropanol) | N/A | 0 | 0 | $1.2 \times 10^1$ | N/A |
| P1 | 0.5 | $1.08 \times 10^5$ | $5.86 \times 10^{-1}$ | $1.85 \times 10^5$ | 22.8 |
| P1 | 1 | $1.00 \times 10^5$ | $5.90 \times 10^{-1}$ | $1.70 \times 10^5$ | 22.9 |
| P1 | 3 | $6.21 \times 10^4$ | $3.41 \times 10^{-1}$ | $1.82 \times 10^5$ | 13.5 |
| P1 | 24 | $5.55 \times 10^4$ | $3.05 \times 10^{-1}$ | $1.82 \times 10^5$ | 12.2 |
| P1 | 48 | $7.23 \times 10^4$ | $5.03 \times 10^{-1}$ | $1.44 \times 10^5$ | 19.6 |
| P2 | 0.5 | $1.00 \times 10^5$ | $6.74 \times 10^{-1}$ | $1.49 \times 10^5$ | 26.1 |
| P2 | 1 | $8.27 \times 10^5$ | 6.66 | $1.24 \times 10^5$ | 252 |
| P2 | 3 | $6.68 \times 10^4$ | $4.79 \times 10^{-1}$ | $1.39 \times 10^5$ | 18.8 |
| P2 | 8 | $6.82 \times 10^4$ | $3.85 \times 10^{-1}$ | $1.77 \times 10^5$ | 15.2 |
| P2 | 24 | $7.63 \times 10^4$ | $4.08 \times 10^{-1}$ | $1.87 \times 10^5$ | 16.1 |
| P2 | 48 | $7.10 \times 10^4$ | $3.63 \times 10^{-1}$ | $1.96 \times 10^5$ | 14.4 |

Example 12

Quantification of Oxidized and Reduced Forms of CoQ10 in Serum

In this experiment, the amounts of oxidized and reduced forms of CoQ10 in serum samples were measured. The samples were spiked with CoQ10-d6 and CoQ10H$_2$-d6 internal standards, and CoQ10 and CoQ10H$_2$ were extracted from each serum sample using a single extraction with 1-propanol, and both CoQ10 and CoQ10H$_2$ were quantified using LC-MS/MS. Chromatographic separation was accomplished using the column Agilent C18 poroshell (2.1µ particle size) and Methanol:1-Propanol 80:20 with 5 mM Ammonium formate as a mobile phase. The mass spectrometric method involved simultaneous quantification of the reduced and oxidized forms of CoQ10 in a single run, accomplished by monitoring the transition of m/z 880 to m/z 197 for the oxidized form of CoQ10, and the transition of m/z 882 to m/z 197 for the reduced form of CoQ10. All samples were handled by using cooled cryoblocks to minimize the oxidation of CoQ10H$_2$. The standard curve was constructed using the samples containing 0, 20, 40, 158, 313, 625, 1250 and 2500 ng/mL of CoQ10 (samples L1, L2, L3, L4, L5, L6, L7 and L8). Also analyzed were standards from the National Institute of Standards and Technology (NIST1, NIST2 and NIST3).

The calculated % accuracy for the measurements of CoQ10 concentration in the samples used for the standard curve ranged from 86.5% to 118% for all samples. The standard curves for the oxidized CoQ10 and reduced CoQ10 (CoQ10H$_2$) and the respresentative chromatograms are shown in FIGS. 10 and 11, respectively, and the raw mass spectrometric data is presented in Table 11 below. All data corresponding to the samples labeled with "ox" are for the oxidized form of CoQ10, and the data corresponding to the samples labeled with "red" correspond to the reduced form of CoQ10. The samples labeled QC1, QC2 and QC3 correspond to quality control samples comprising serum spiked with CoQ10 from a lot that is different from the one used to prepare the samples for the standard curve.

samples were spiked with CoQ10-d6 and CoQ10H$_2$-d6 internal standards, and CoQ10 and CoQ10H$_2$ were extracted from each plasma sample using extraction with hexane and 1-propanol, and both CoQ10 and CoQ10H$_2$ were quantified using LC-MS/MS. Chromatographic separation was accomplished using the column Agilent C18 poroshell (2.1μ particle size) and Methanol:1-Propanol 80:20 with 5 mM Ammonium formate as a mobile phase. The mass spectrometric method involved simultaneous quantification of the reduced and oxidized forms of CoQ10 in a single run, accomplished by monitoring the transition of m/z 880 to m/z 197 for the oxidized form of CoQ10, and the transition of m/z 882 to m/z 197 for the reduced form of CoQ10. All samples were handled by using cooled cryoblocks to minimize the oxidation of

TABLE 11

Raw data for quantification of oxidized and reduced forms of CoQ10 in serum.

| Sample Name | Sample Type | Analyte Peak Area (counts) | Analyte Peak Height (cps) | Analyte Concentration (ng/mL) | IS Peak Area (counts) | IS Peak Height (cps) | Calculated Concentration (ng/mL) | Accuracy (%) |
|---|---|---|---|---|---|---|---|---|
| Solvent | Solvent | 0 | 0 | 0 | 0 | 0 | N/A | N/A |
| Solvent | Solvent | 8.53 × 10$^3$ | 7.08 × 10$^2$ | 0 | 0 | 0 | N/A | N/A |
| Solvent | Solvent | 0 | 0 | 0 | 0 | 0 | N/A | N/A |
| Solvent | Solvent | 0 | 0 | 0 | 0 | 0 | N/A | N/A |
| Solvent | Solvent | 0 | 0 | 0 | 0 | 0 | N/A | N/A |
| Solvent | Solvent | 0 | 0 | 0 | 0 | 0 | N/A | N/A |
| L1-ox | Standard | 4.37 × 10$^4$ | 4.10 × 10$^3$ | 20 | 1.02 × 10$^6$ | 9.52 × 10$^4$ | 19.1 | 95.3 |
| L1-red | Standard | 4.34 × 10$^3$ | 5.71 × 10$^2$ | 20 | 2.29 × 10$^5$ | 2.79 × 10$^4$ | 23.6 | 118 |
| L2-ox | Standard | 4.50 × 10$^4$ | 4.22 × 10$^3$ | 40 | 9.10 × 10$^5$ | 8.32 × 10$^4$ | 38.4 | 96.1 |
| L2-red | Standard | 6.28 × 10$^3$ | 7.67 × 10$^2$ | 40 | 2.10 × 10$^5$ | 2.56 × 10$^4$ | 40.8 | 102 |
| L3-ox | Unknown | 5.23 × 10$^4$ | 5.09 × 10$^3$ | N/A | 9.73 × 10$^5$ | 9.08 × 10$^4$ | 51.4 | N/A |
| L3-red | Unknown | 1.01 × 10$^4$ | 1.21 × 10$^3$ | N/A | 2.16 × 10$^5$ | 2.61 × 10$^4$ | 67.1 | N/A |
| L4-ox | Standard | 8.10 × 10$^4$ | 7.70 × 10$^3$ | 158 | 8.80 × 10$^5$ | 8.17 × 10$^4$ | 165 | 104 |
| L4-red | Standard | 1.92 × 10$^4$ | 2.36 × 10$^3$ | 158 | 2.11 × 10$^5$ | 2.56 × 10$^4$ | 137 | 86.5 |
| L5-ox | Standard | 1.23 × 10$^5$ | 1.18 × 10$^4$ | 313 | 8.48 × 10$^5$ | 7.77 × 10$^4$ | 321 | 103 |
| L5-red | Standard | 3.50 × 10$^4$ | 4.14 × 10$^3$ | 313 | 1.91 × 10$^5$ | 2.30 × 10$^4$ | 281 | 89.9 |
| L6-ox | Standard | 2.08 × 10$^5$ | 1.94 × 10$^4$ | 625 | 8.17 × 10$^5$ | 7.53 × 10$^4$ | 649 | 104 |
| L6-red | Standard | 7.08 × 10$^4$ | 8.25 × 10$^3$ | 625 | 1.78 × 10$^5$ | 2.10 × 10$^4$ | 619 | 99 |
| L7-ox | Standard | 3.77 × 10$^5$ | 3.52 × 10$^4$ | 1250 | 8.36 × 10$^5$ | 7.85 × 10$^4$ | 1230 | 98.4 |
| L7-red | Standard | 1.58 × 10$^5$ | 1.92 × 10$^4$ | 1250 | 1.90 × 10$^5$ | 2.27 × 10$^4$ | 1310 | 105 |
| L8-ox | Standard | 7.57 × 10$^5$ | 6.99 × 10$^4$ | 2500 | 8.68 × 10$^5$ | 8.01 × 10$^4$ | 2480 | 99/3 |
| L8-red | Standard | 3.16 × 10$^5$ | 3.82 × 10$^4$ | 2500 | 1.98 × 10$^5$ | 2.40 × 10$^4$ | 2500 | 99.9 |
| Solvent | Solvent | 0 | 0 | 0 | 0 | 0 | N/A | N/A |
| Solvent | Solvent | 0 | 0 | 0 | 0 | 0 | N/A | N/A |
| QC1-ox | Quality control | 5.75 × 10$^4$ | 5.39 × 10$^3$ | 63 | 8.52 × 10$^5$ | 8.00 × 10$^4$ | 92.3 | 147 |
| QC1-red | Quality control | 8.85 × 10$^3$ | 1.10 × 10$^3$ | 63 | 1.83 × 10$^5$ | 2.21 × 10$^4$ | 69.8 | 111 |
| QC2-ox | Quality control | 1.17 × 10$^5$ | 1.20 × 10$^4$ | 250 | 8.75 × 10$^5$ | 8.05 × 10$^4$ | 288 | 115 |
| QC2-red | Quality control | 3.52 × 10$^4$ | 4.21 × 10$^3$ | 250 | 1.98 × 10$^5$ | 2.37 × 10$^4$ | 274 | 110 |
| QC3-ox | Quality control | 3.76 × 10$^5$ | 3.44 × 10$^4$ | 1250 | 7.80 × 10$^5$ | 7.20 × 10$^4$ | 1330 | 106 |
| QC3-red | Quality control | 1.89 × 10$^5$ | 2.26 × 10$^4$ | 1250 | 2.33 × 10$^5$ | 2.75 × 10$^4$ | 1270 | 102 |
| Solvent | Solvent | 0 | 0 | 0 | 0 | 0 | N/A | N/A |
| Solvent | Solvent | 0 | 0 | 0 | 0 | 0 | N/A | N/A |
| NIST1-ox | Unknown | 3.19 × 10$^5$ | 3.01 × 10$^4$ | N/A | 8.49 × 10$^5$ | 8.05 × 10$^4$ | 1010 | N/A |
| NIST1-red | Unknown | 1.97 × 10$^4$ | 1.88 × 10$^3$ | N/A | 1.90 × 10$^5$ | 2.30 × 10$^4$ | 157 | N/A |
| NIST2-ox | Unknown | 3.43 × 10$^5$ | 3.23 × 10$^4$ | N/A | 8.37 × 10$^5$ | 7.82 × 10$^4$ | 1110 | N/A |
| NIST2-red | Unknown | 2.22 × 10$^4$ | 2.10 × 10$^3$ | N/A | 2.05 × 10$^5$ | 2.45 × 10$^4$ | 165 | N/A |
| NIST3-ox | Unknown | 4.79 × 10$^5$ | 4.50 × 10$^4$ | N/A | 8.07 × 10$^5$ | 7.54 × 10$^4$ | 1650 | N/A |
| NIST3-red | Unknown | 3.11 × 10$^4$ | 2.92 × 10$^3$ | N/A | 2.10 × 10$^5$ | 2.57 × 10$^4$ | 227 | N/A |
| Solvent | Solvent | 0 | 0 | 0 | 0 | 0 | N/A | N/A |
| Solvent | Solvent | 0 | 0 | 0 | 0 | 0 | N/A | N/A |

Example 13

Quantification of Oxidized and Reduced Forms of CoQ10 in Plasma

In this experiment, the amounts of oxidized and reduced forms of CoQ10 in plasma samples were measured. The CoQ10H$_2$. The standard curve was constructed using the samples containing 0, 20, 158, 625, 1250 and 2500 ng/mL of CoQ10 (samples L1, L2, L3, L4, L5, L6, L7 and L8). The calculated % accuracy for the measurements of CoQ10 concentration in the samples used for the standard curve ranged from 84.8% to 119% for all samples. The standard curves and the representative chromatograms for the oxidized CoQ10 and reduced CoQ10 (CoQ10H$_2$) are shown in FIGS. 12 and 13, respectively, and the raw mass spectrometric data is presented in Table 12 below. All data corresponding to the samples labeled with "ox" are for the oxidized form of CoQ10, and the data corresponding to the samples labeled with "red" correspond to the reduced form of CoQ10. The samples labeled QC1, QC2, QC3 and QC4 correspond to quality control samples comprising plasma spiked with CoQ10 from a lot that is different from the one used to prepare the samples for the standard curve.

TABLE 12

Raw data for quantification of oxidized and reduced forms of CoQ10 in plasma.

| Sample Name | Sample Type | Analyte Peak Area (counts) | Analyte Peak Height (cps) | Analyte Concentration (ng/mL) | IS Peak Area (counts) | IS Peak Height (cps) | Calculated Concentration (ng/mL) | Accuracy (%) |
|---|---|---|---|---|---|---|---|---|
| Solvent | Solvent | 0 | 0 | 0 | 0 | 0 | N/A | N/A |
| Solvent | Solvent | 0 | 0 | 0 | 0 | 0 | N/A | N/A |
| L1-ox | Standard | $1.88 \times 10^5$ | $1.72 \times 10^3$ | 20 | $9.38 \times 10^5$ | $8.32 \times 10^4$ | 23.8 | 119 |
| L1-red | Standard | $6.77 \times 10^4$ | $7.88 \times 10^4$ | 20 | $3.36 \times 10^5$ | $3.92 \times 10^4$ | 19.6 | 98.1 |
| L2-ox | Standard | $1.77 \times 10^5$ | $1.61 \times 10^3$ | N/A | $8.80 \times 10^5$ | $7.82 \times 10^4$ | 26.1 | N/A |
| L2-red | Standard | $6.94 \times 10^4$ | $8.06 \times 10^4$ | N/A | $3.13 \times 10^5$ | $3.68 \times 10^4$ | 46.6 | N/A |
| L3-ox | Unknown | $1.65 \times 10^5$ | $1.49 \times 10^4$ | N/A | $6.75 \times 10^5$ | $5.94 \times 10^4$ | 130 | N/A |
| L3-red | Unknown | $9.19 \times 10^4$ | $1.09 \times 10^4$ | N/A | $3.50 \times 10^5$ | $4.15 \times 10^4$ | 101 | N/A |
| L4-ox | Standard | $1.93 \times 10^5$ | $1.77 \times 10^4$ | 158 | $7.87 \times 10^5$ | $7.02 \times 10^4$ | 134 | 84.8 |
| L4-red | Standard | $8.64 \times 10^4$ | $1.04 \times 10^4$ | 158 | $2.79 \times 10^5$ | $3.36 \times 10^4$ | 165 | 104 |
| L5-ox | Standard | $2.44 \times 10^5$ | $2.25 \times 10^4$ | N/A | $8.54 \times 10^5$ | $7.70 \times 10^4$ | 230 | N/A |
| L5-red | Standard | $1.14 \times 10^5$ | $1.35 \times 10^4$ | N/A | $2.99 \times 10^5$ | $3.57 \times 10^4$ | 260 | N/A |
| L6-ox | Standard | $3.57 \times 10^5$ | $3.24 \times 10^4$ | 625 | $8.18 \times 10^5$ | $7.43 \times 10^4$ | 598 | 95.7 |
| L6-red | Standard | $1.83 \times 10^5$ | $2.25 \times 10^4$ | 625 | $2.88 \times 10^5$ | $3.47 \times 10^4$ | 601 | 96.1 |
| L7-ox | Standard | $5.73 \times 10^5$ | $5.32 \times 10^4$ | 1250 | $8.30 \times 10^5$ | $7.63 \times 10^4$ | 1210 | 97 |
| L7-red | Standard | $3.20 \times 10^5$ | $3.91 \times 10^4$ | 1250 | $2.82 \times 10^5$ | $3.33 \times 10^4$ | 1270 | 101 |
| L8-ox | Standard | $9.97 \times 10^5$ | $9.38 \times 10^4$ | 2500 | $7.94 \times 10^5$ | $7.14 \times 10^4$ | 2580 | 103 |
| L8-red | Standard | $5.95 \times 10^5$ | $7.08 \times 10^4$ | 2500 | $2.90 \times 10^5$ | $3.48 \times 10^4$ | 2500 | 100 |
| Solvent | Solvent | 0 | 0 | 0 | 0 | 0 | N/A | N/A |
| Solvent | Solvent | 0 | 0 | 0 | 0 | 0 | N/A | N/A |
| Solvent | Solvent | 0 | 0 | 0 | 0 | 0 | N/A | N/A |
| Solvent | Solvent | 0 | 0 | 0 | 0 | 0 | N/A | N/A |
| QC1-ox | Quality control | $2.04 \times 10^5$ | $1.83 \times 10^4$ | 125 | $7.92 \times 10^5$ | $7.21 \times 10^4$ | 164 | 131 |
| QC1-red | Quality control | $9.85 \times 10^4$ | $1.15 \times 10^4$ | 125 | $3.23 \times 10^5$ | $3.83 \times 10^4$ | 158 | 126 |
| QC2-ox | Quality control | $2.21 \times 10^5$ | $1.98 \times 10^4$ | 250 | $7.20 \times 10^5$ | $6.49 \times 10^4$ | 283 | 113 |
| QC2-red | Quality control | $1.40 \times 10^5$ | $1.66 \times 10^4$ | 250 | $3.65 \times 10^5$ | $4.30 \times 10^4$ | 263 | 105 |
| QC3-ox | Quality control | $5.61 \times 10^5$ | $5.06 \times 10^4$ | 1250 | $7.82 \times 10^5$ | $7.19 \times 10^4$ | 1280 | 102 |
| QC3-red | Quality control | $3.86 \times 10^5$ | $4.65 \times 10^4$ | 1250 | $3.93 \times 10^5$ | $4.83 \times 10^4$ | 1070 | 85.3 |
| QC4-ox | Quality control | $1.15 \times 10^6$ | $1.04 \times 10^5$ | 2500 | $9.09 \times 10^5$ | $8.18 \times 10^4$ | 2610 | 104 |
| QC4-red | Quality control | $6.16 \times 10^5$ | $7.51 \times 10^4$ | 2500 | $3.13 \times 10^5$ | $3.69 \times 10^4$ | 2380 | 95.3 |

IV. EQUIVALENTS

Those skilled in the art will recognize, or be able to ascertain using no more than routine experimentation, many equivalents to the specific embodiments of the invention described herein. Such equivalents are intended to be encompassed by the following claims.

V. RELATED REFERENCES

All publications and patent documents cited in this application are incorporated by reference in pertinent part for all purposes to the same extent as if each individual publication or patent document were so individually denoted. By their citation of various references in this document, Applicants do not admit any particular reference is "prior art" to their disclosure. It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims and their equivalents.

All figures are offered by way of illustration, not by way of limitation. While specific examples have been provided, the descriptions are illustrative and not restrictive. Any one or more of the features of the previously described embodiments can be combined in any manner with one or more features of any other embodiments in the present disclosure. Furthermore, many variations of the present disclosure will become apparent to those skilled in the art upon review of this disclosure.

What is claimed is:

1. A method for determining the amount of coenzyme Q10 (CoQ10) in a sample, the method comprising
   adding a first extraction buffer and a second extraction buffer to the sample that results in phase separation of the sample, thereby forming a first extraction buffer layer and a second extraction buffer layer; and analyzing the second extraction buffer layer to determine the amount of CoQ10;
   wherein the sample comprises tissues, cells collected from a bodily fluid or cell lines; and wherein the first extraction buffer comprises a surfactant, a mild detergent or a steroid acid.

2. The method of claim 1, the method comprising
adding a first extraction buffer and a second extraction buffer to the sample that results in phase separation of the sample, thereby forming a first extraction buffer layer and a second extraction buffer layer;
mixing the sample; and
analyzing the second extraction buffer layer to determine the amount of CoQ10, wherein a single extraction with the first extraction buffer and the second extraction buffer results in detecting an at least 2-fold greater amount of CoQ10 than using methanol-only extraction.

3. The method of claim 1, the method comprising
adding a first extraction buffer to the sample;
heating and mixing the sample;
adding a second extraction buffer to the sample that results in phase separation of the sample, thereby forming a first extraction buffer layer and a second extraction buffer layer;
heating and mixing the sample;
cooling the sample to ambient temperature; and
analyzing the second extraction buffer layer to determine the amount of CoQ10 in the sample.

4. The method of claim 2, the method comprising
adding a first extraction buffer to the sample;
heating and mixing the sample;
adding a second extraction buffer to the sample that results in phase separation of the sample, thereby forming a first extraction buffer layer and a second extraction buffer layer;
heating and mixing the sample;
cooling the sample to ambient temperature; and
analyzing spectroscopically by spectroscopic analysis the second extraction buffer layer to determine the amount of CoQ10 in the sample, wherein a single extraction with the extraction buffer results in extracting at least 2-fold greater amount of CoQ10 than using methanol-only extraction followed by Liquid chromatography/mass spectrometry/mass spectrometry (LC/MS/MS).

5. The method of claim 1, wherein the amount of CoQ10 detected in the sample is determined spectroscopically by spectroscopic analysis or wherein the amount of CoQ10 is detected using LC/MS/MS.

6. The method of claim 2, wherein the amount of CoQ10 extracted using a first extraction buffer and a second extraction buffer is determined spectroscopically, and the amount of CoQ10 detected using methanol-only extraction is determined using LC/MS/MS.

7. The method of claim 1, wherein the method is part of a high throughput screening analysis method and wherein the entire method is carried out by automation.

8. The method of claim 1, wherein the total amount of CoQ10 detected in the sample, wherein the sample is extracted using a first extraction buffer and a second extraction buffer and the amount of CoQ10 is determined spectroscopically, is at least 2-fold greater than the total amount of CoQ10 detected using methanol-only extraction followed by LC/MS/MS CoQ10 detection.

9. The method of claim 1, wherein the second extraction buffer comprises a non-polar solvent or an organic solvent.

10. The method of claim 9, wherein the second extraction buffer comprises a solvent selected from the group consisting of benzene, toluene, xylene, hexane, heptane, octane, cyclohexane, 1,4-dioxane, chloroform, diethyl ether, diisopropyl ether, and diisobutyl ether, carbon tetrachloride, dimethyl formamide (DMF), chloromethane, dichloromethane, and wherein the second extraction buffer comprises an alkane, acetonitrile or isopropanol.

11. The method of claim 1, wherein the first extraction buffer comprises a polar protic solvent or an organic solvent or wherein the first extraction buffer is an aqueous solution.

12. The method of claim 11, wherein the first extraction buffer comprises a solvent selected from the group consisting of formic acid, n-butanol, isopropanol, n-propanol, ethanol, methanol, acetic acid, trichloroacetic acid (TCA), water or wherein the solvent comprises an alcohol.

13. The method of claim 1, wherein the detergent is a mild detergent.

14. The method according to claim 1, wherein the steroid acid is a bile acid.

15. The method according to claim 14, wherein the bile acid comprises an acid selected from the group consisting of taurochloric acid, glycocholic acid, cholic acid, chenodeoxycholic acid, deoxycholic acid, and lithocholic acid.

16. The method according to claim 14, wherein the bile acid comprises deoxycholic acid and wherein the deoxycholic acid is a salt.

17. The method according to claim 16, wherein the deoxycholic acid salt comprises an inorganic ion that is a group I metal.

18. The method according to claim 17, wherein the inorganic ion of the deoxycholic acid salt comprises an inorganic ion that is a salt selected from the group consisting of $Li^+$, $Na^+$, and $K^+$.

19. The method of claim 1, wherein the sample comprises a biological sample.

20. The method according to claim 19, wherein the biological sample is a cell based sample or wherein the sample comprises a mammalian sample or amphibian sample.

21. The method of claim 20, wherein the sample comprises a sample selected from the group consisting of a human sample, a non-human primate sample, and a rodent sample.

22. The method of claim 21, wherein the sample is a sample from a subject selected from mouse, rat, guinea pig, rabbit, and human.

23. The method of claim 5, wherein the spectroscopic analysis carried out by using a spectroscopic technique selected from absorption spectroscopy, fluorescence X-ray spectroscopy, flame spectroscopy, visible spectroscopy, ultraviolet spectroscopy, infrared spectroscopy, near infrared spectroscopy, Raman spectroscopy, coherent anti-Stokes Raman Spectroscopy (CARS), nuclear magnetic resonance spectroscopy, photoemission spectroscopy, and Mossbauer spectroscopy.

24. The method according to claim 23, wherein the spectroscopic technique is ultraviolet spectroscopy.

25. The method according to claim 23, wherein the ultraviolet spectroscopy is performed at one or more wavelengths between 270 nm to 280 nm.

26. The method of claim 1, wherein the ratio of the volume of the first extraction buffer to the volume of the second extraction buffer is 5:1 to 1:1.

27. The method of claim 1, wherein the ratio of the surfactant or detergent to the volume of the first extraction buffer is 50:1 to 1:1.

28. The method of claim 1, wherein the sample is heated to the temperature of 50-100° C. after addition of the first extraction buffer, second extraction buffer, or both the first and second extraction buffer.

29. The method of claim 28, wherein the sample is heated to the same temperature after addition of the first extraction buffer and the second extraction buffer.

30. The method of claim 28, wherein the sample is heated to different temperatures after addition of the first extraction buffer and the second extraction buffer.

31. The method of claim 28, wherein the heating is for a time of at least 5 seconds, at least 10 seconds, at least 15 seconds, at least 20 seconds, at least 30 seconds, at least 40 seconds, at least 50 seconds, at least 60 seconds, at least 75 seconds, at least 90 seconds, at least 105 seconds, or at least 120 seconds.

32. The method of claim 28, wherein the sample is heated for the same amount of time after addition of the first extraction buffer and the second extraction buffer.

33. The method of claim 28, wherein the sample is heated for different amounts of time after addition of the first extraction buffer and the second extraction buffer.

34. The method of claim 28, wherein heating the sample increases the extraction of CoQ10 by at least 5%, at least 10%, at least 15%, at least 20%, at least 25%, at least 30%, or at least 50% as compared to a control sample that was not heated.

35. The method of claim 2, wherein the sample is mixed by mechanical stirring, sonication or magnetic stirring.

36. The method of claim 35, wherein the sample is mixed after the addition of the first extraction buffer and/or after the addition of the second extraction buffer.

37. The method of claim 4, wherein the sample is filtered prior to spectroscopic analysis of the second extraction buffer.

38. The method of claim 1, wherein the entire method is completed within 10 minutes, within 5 minutes, within 1 minute or within 30 seconds.

39. A kit for practicing the method of claim 1.

40. A method for determining the amount of coenzyme Q10 (CoQ10) in a sample, the method comprising
adding a first extraction buffer and a second extraction buffer to the sample that results in phase separation of the sample, thereby forming a first extraction buffer layer and a second extraction buffer layer; and analyzing the second extraction buffer layer to determine the amount of CoQ10;
wherein an inorganic salt or a saturated brined solution is added to the sample after addition of the second extraction buffer.

41. The method of claim 40, the method comprising
adding a first extraction buffer and a second extraction buffer to the sample that results in phase separation of the sample, thereby forming a first extraction buffer layer and a second extraction buffer layer;
mixing the sample; and
analyzing the second extraction buffer layer to determine the amount of CoQ10, wherein a single extraction with the first extraction buffer and the second extraction buffer results in detecting an at least 2-fold greater amount of CoQ10 than using methanol-only extraction.

42. The method of claim 40, the method comprising
adding a first extraction buffer to the sample;
heating and mixing the sample;
adding a second extraction buffer to the sample that results in phase separation of the sample, thereby forming a first extraction buffer layer and a second extraction buffer layer;
heating and mixing the sample;
cooling the sample to ambient temperature; and
analyzing the second extraction buffer layer to determine the amount of CoQ10 in the sample.

43. The method of claim 41, the method comprising
adding a first extraction buffer to the sample;
heating and mixing the sample;
adding a second extraction buffer to the sample that results in phase separation of the sample, thereby forming a first extraction buffer layer and a second extraction buffer layer;
heating and mixing the sample;
cooling the sample to ambient temperature; and
analyzing spectroscopically by spectroscopic analysis the second extraction buffer layer to determine the amount of CoQ10 in the sample, wherein a single extraction with the extraction buffer results in extracting at least 2-fold greater amount of CoQ10 than using methanol-only extraction followed by liquid chromatography/mass spectrometry/mass spectrometry (LC/MS/MS).

44. The method of claim 40, wherein the amount of CoQ10 detected in the sample is determined spectroscopically by spectroscopic analysis or wherein the amount of CoQ10 is detected using LC/MS/MS.

45. The method of claim 41, wherein the amount of CoQ10 extracted using a first extraction buffer and a second extraction buffer is determined spectroscopically, and the amount of CoQ10 detected using methanol-only extraction is determined using LC/MS/MS.

46. The method of claim 40, wherein the method is part of a high throughput screening analysis method and wherein the entire method is carried out by automation.

47. The method of claim 40, wherein the total amount of CoQ10 detected in the sample, wherein the sample is extracted using a first extraction buffer and a second extraction buffer and the amount of CoQ10 is determined spectroscopically, is at least 2-fold greater than the total amount of CoQ10 detected using methanol-only extraction followed by LC/MS/MS CoQ10 detection.

48. The method of claim 40, wherein the second extraction buffer comprises a non-polar solvent or an organic solvent.

49. The method of claim 48, wherein the second extraction buffer comprises a solvent selected from the group consisting of benzene, toluene, xylene, hexane, heptane, octane, cyclohexane, 1,4-dioxane, chloroform, diethyl ether, diisopropyl ether, and diisobutyl ether, carbon tetrachloride, dimethyl formamide (DMF), chloromethane, dichloromethane, and wherein the second extraction buffer comprises an alkane, acetonitrile or isopropanol.

50. The method of claim 40, wherein the first extraction buffer comprises a polar protic solvent or an organic solvent or wherein the first extraction buffer is an aqueous solution.

51. The method of claim 50, wherein the first extraction buffer comprises a solvent selected from the group consisting of formic acid, n-butanol, isopropanol, n-propanol, ethanol, methanol, acetic acid, trichloroacetic acid (TCA), water or wherein the solvent comprises an alcohol.

52. The method of claim 40, wherein the sample comprises a biological sample.

53. The method according to claim 52, wherein the biological sample is a cell based sample or wherein the sample comprises a mammalian sample or amphibian sample.

54. The method of claim 53, wherein the sample comprises a sample selected from the group consisting of a human sample, a non-human primate sample, and a rodent sample.

55. The method of claim 54, wherein the sample is a sample from a subject selected from mouse, rat, guinea pig, rabbit, and human.

56. The method of claim 44, wherein the spectroscopic analysis carried out by using a spectroscopic technique selected from absorption spectroscopy, fluorescence X-ray spectroscopy, flame spectroscopy, visible spectroscopy, ultraviolet spectroscopy, infrared spectroscopy, near infrared spectroscopy, Raman spectroscopy, coherent anti-Stokes Raman Spectroscopy (CARS), nuclear magnetic resonance spectroscopy, photoemission spectroscopy, and Mossbauer spectroscopy.

57. The method according to claim 56, wherein the spectroscopic technique is ultraviolet spectroscopy.

58. The method according to claim 57, wherein the ultraviolet spectroscopy is performed at one or more wavelengths selected from 270 nm to 280 nm.

59. The method of claim 40, wherein the ratio of the volume of the first extraction buffer to the volume of the second extraction buffer is 5:1 to 1:1.

60. The method of claim 40, wherein the sample is heated to the temperature of 50-100° C. after addition of the first extraction buffer, second extraction buffer, or both the first and second extraction buffer.

61. The method of claim 60, wherein the sample is heated to the same temperature after addition of the first extraction buffer and the second extraction buffer.

62. The method of claim 60, wherein the sample is heated to different temperatures after addition of the first extraction buffer and the second extraction buffer.

63. The method of claim 60, wherein the heating is for a time of at least 5 seconds, at least 10 seconds, at least 15 seconds, at least 20 seconds, at least 30 seconds, at least 40 seconds, at least 50 seconds, at least 60 seconds, at least 75 seconds, at least 90 seconds, at least 105 seconds, or at least 120 seconds.

64. The method of claim 60, wherein the sample is heated for the same amount of time after addition of the first extraction buffer and the second extraction buffer.

65. The method of claim 60, wherein the sample is heated for different amounts of time after addition of the first extraction buffer and the second extraction buffer.

66. The method of claim 60, wherein heating the sample increases the extraction of CoQ10 by at least 5%, at least 10%, at least 15%, at least 20%, at least 25%, at least 30%, or at least 50% as compared to a control sample that was not heated.

67. The method of claim 41, wherein the sample is mixed by mechanical stirring, sonication or magnetic stirring.

68. The method of claim 67, wherein the sample is mixed after the addition of the first extraction buffer and/or after the addition of the second extraction buffer.

69. The method of claim 43, wherein the sample is filtered prior to spectroscopic analysis of the second extraction buffer.

70. The method of claim 40, wherein the entire method is completed within 10 minutes, within 5 minutes, within 1 minute or within 30 seconds.

71. A kit for practicing the method of claim 40.

72. The method of claim 70, wherein the sample comprises tissues, cells collected from a bodily fluid or cell lines.

73. The method according to claim 25, wherein the ultraviolet spectroscopy is performed at one or more wavelengths between 273 nm to 277 nm.

74. The method according to claim 73, wherein the ultraviolet spectroscopy is performed at wavelength of 275 nm.

75. The method according to claim 58, wherein the ultraviolet spectroscopy is performed at one or more wavelengths between 273 nm to 277 nm.

76. The method according to claim 75, wherein the ultraviolet spectroscopy is performed at wavelength of 275 nm.

77. The method of claim 28, wherein the sample is heated to the temperature of 55-75° C. after addition of the first extraction buffer, second extraction buffer, or both the first and second extraction buffer.

78. The method of claim 77, wherein the sample is heated to the temperature of 60-70° C. after addition of the first extraction buffer, second extraction buffer, or both the first and second extraction buffer.

79. The method of claim 78, wherein the sample is heated to the temperature of 65° C. after addition of the first extraction buffer, second extraction buffer, or both the first and second extraction buffer.

80. The method of claim 60, wherein the sample is heated to the temperature of 55-75° C. after addition of the first extraction buffer, second extraction buffer, or both the first and second extraction buffer.

81. The method of claim 80, wherein the sample is heated to the temperature of 60-70° C. after addition of the first extraction buffer, second extraction buffer, or both the first and second extraction buffer.

82. The method of claim 81, wherein the sample is heated to the temperature of 65° C. after addition of the first extraction buffer, second extraction buffer, or both the first and second extraction buffer.

* * * * *